(12) United States Patent
Wallace

(10) Patent No.: US 11,654,024 B1
(45) Date of Patent: May 23, 2023

(54) HEART VALVE CLIP

(71) Applicant: Capstan Medical Inc., Santa Cruz, CA (US)

(72) Inventor: Daniel T. Wallace, Santa Cruz, CA (US)

(73) Assignee: CAPSTAN MEDICAL INC., Santa Cruz, CA (US)

( * ) Notice: Subject to any disclaimer, the term of this patent is extended or adjusted under 35 U.S.C. 154(b) by 0 days.

(21) Appl. No.: 17/992,693

(22) Filed: Nov. 22, 2022

Related U.S. Application Data

(60) Provisional application No. 63/381,698, filed on Oct. 31, 2022.

(51) Int. Cl.
A61F 2/24 (2006.01)

(52) U.S. Cl.
CPC .... *A61F 2/2454* (2013.01); *A61F 2220/0008* (2013.01); *A61F 2220/0075* (2013.01)

(58) Field of Classification Search
CPC ............ A61F 2/2454; A61F 2220/0008; A61F 2220/0075
See application file for complete search history.

(56) References Cited

U.S. PATENT DOCUMENTS

| | | | |
|---|---|---|---|
| 6,752,813 B2 | 6/2004 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,736,388 B2 | 6/2010 | Goldfarb et al. |
| 8,029,518 B2 | 10/2011 | Goldfarb et al. |
| 8,057,493 B2 | 11/2011 | Goldfarb et al. |
| 8,187,299 B2 | 5/2012 | Goldfarb et al. |
| 8,343,174 B2 | 1/2013 | Goldfarb et al. |
| 8,470,028 B2 | 6/2013 | Thornton et al. |
| 8,500,761 B2 | 8/2013 | Goldfarb et al. |
| 8,740,920 B2 | 6/2014 | Goldfarb et al. |
| 9,044,246 B2 | 6/2015 | Goldfarb et al. |
| 9,060,858 B2 | 6/2015 | Thornton et al. |
| 9,510,829 B2 | 12/2016 | Goldfarb et al. |
| 10,076,415 B1 | 9/2018 | Metchik et al. |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |

(Continued)

*Primary Examiner* — Suzette J Gherbi
(74) *Attorney, Agent, or Firm* — Polsinelli PC

(57) ABSTRACT

A valve repair device, e.g., for treating mitral valve regurgitation, includes a tubular body defining a longitudinal axis, paddles supported by the tubular body and movable to change abduction of the paddles relative to the longitudinal axis, and retention members supported by the tubular body proximal the paddles and similarly movable to change abduction of the retention members relative to the longitudinal axis to facilitate capture of native valve leaflets between pairs of paddles and retention members. Movement of the paddles and/or retention members is provided by one or more control mechanisms including a collar a shaft extending within the tubular body. Each shaft is threadedly engaged to a respective collar and coupled to one or more of the movable elements such that, when the collar is rotated, the shaft translates to change abduction of the movable element relative to the longitudinal axis.

20 Claims, 30 Drawing Sheets

(56) References Cited

U.S. PATENT DOCUMENTS

| | | | |
|---|---|---|---|
| 10,136,993 | B1 | 11/2018 | Metchik et al. |
| 10,159,570 | B1 | 12/2018 | Metchik et al. |
| 10,231,837 | B1 | 3/2019 | Metchik et al. |
| 10,238,493 | B1 | 3/2019 | Metchik et al. |
| 10,245,144 | B1 | 4/2019 | Metchik et al. |
| 10,507,108 | B2 | 12/2019 | Delgado et al. |
| 10,507,109 | B2 | 12/2019 | Metchik et al. |
| 10,524,913 | B2 | 1/2020 | Delgado et al. |
| 10,595,997 | B2 | 3/2020 | Metchik et al. |
| 10,624,618 | B2 | 4/2020 | Goldfarb et al. |
| 10,631,871 | B2 | 4/2020 | Goldfarb et al. |
| 10,646,229 | B2 | 5/2020 | Goldfarb et al. |
| 10,653,427 | B2 | 5/2020 | Goldfarb et al. |
| 10,667,804 | B2 | 6/2020 | Basude et al. |
| 10,667,823 | B2 | 6/2020 | Goldfarb et al. |
| 10,667,911 | B2 | 6/2020 | Ketai et al. |
| 10,667,912 | B2 | 6/2020 | Dixon et al. |
| 10,813,760 | B2 | 10/2020 | Metchik et al. |
| 10,828,042 | B2 | 11/2020 | Goldfarb et al. |
| 10,842,627 | B2 | 11/2020 | Delgado et al. |
| 10,849,754 | B2 | 12/2020 | Delgado et al. |
| 10,869,763 | B2 | 12/2020 | Delgado et al. |
| 10,874,514 | B2 | 12/2020 | Dixon et al. |
| 10,888,425 | B2 | 1/2021 | Delgado et al. |
| 10,898,327 | B2 | 1/2021 | Dixon et al. |
| 10,905,553 | B2 | 2/2021 | Delgado et al. |
| 10,918,482 | B2 | 2/2021 | Delgado et al. |
| 10,918,483 | B2 | 2/2021 | Metchik et al. |
| 10,925,732 | B2 | 2/2021 | Delgado et al. |
| 10,925,733 | B2 | 2/2021 | Delgado et al. |
| 10,925,734 | B2 | 2/2021 | Delgado et al. |
| 10,925,735 | B2 | 2/2021 | Metchik et al. |
| 10,932,908 | B2 | 3/2021 | Dixon et al. |
| 10,940,005 | B2 | 3/2021 | Dixon et al. |
| 10,945,843 | B2 | 3/2021 | Delgado et al. |
| 10,945,844 | B2 | 3/2021 | McCann et al. |
| 10,952,853 | B2 | 3/2021 | Delgado et al. |
| 10,959,847 | B2 | 3/2021 | Metchik et al. |
| 10,959,848 | B2 | 3/2021 | Delgado et al. |
| 10,973,639 | B2 | 4/2021 | Metchik et al. |
| 10,987,221 | B2 | 4/2021 | McCann et al. |
| 10,993,809 | B2 | 5/2021 | McCann et al. |
| 11,000,373 | B2 | 5/2021 | Delgado et al. |
| 11,000,375 | B2 | 5/2021 | McCann et al. |
| 11,013,598 | B2 * | 5/2021 | Metchik ............ A61B 17/0643 |
| 11,013,601 | B2 | 5/2021 | Delgado et al. |
| 11,020,229 | B2 * | 6/2021 | Delgado ............... A61F 2/2457 |
| 11,039,925 | B2 | 6/2021 | Metchik et al. |
| 11,058,539 | B2 * | 7/2021 | Dixon .................. A61F 2/2466 |
| 11,083,582 | B2 | 8/2021 | McCann et al. |
| 11,096,784 | B2 * | 8/2021 | Dixon .................. A61F 2/2436 |
| 11,129,717 | B2 | 9/2021 | McCann et al. |
| 11,147,672 | B2 | 10/2021 | McCann et al. |
| 11,179,240 | B2 * | 11/2021 | Delgado ............... A61F 2/2418 |
| 11,202,710 | B2 | 12/2021 | McCann et al. |
| 11,207,181 | B2 | 12/2021 | Freschauf et al. |
| 11,224,511 | B2 * | 1/2022 | Dixon .................... A61F 2/246 |
| 11,234,822 | B2 * | 2/2022 | Dixon ................ A61B 17/1227 |
| 11,298,228 | B2 * | 4/2022 | Metchik ............... A61F 2/2463 |
| 2012/0143304 | A1 * | 6/2012 | Wubbeling ............. A61F 2/966 |
| | | | 29/446 |
| 2014/0214155 | A1 * | 7/2014 | Kelley ...................... A61F 2/95 |
| | | | 623/2.11 |
| 2023/0040083 | A1 * | 2/2023 | Gifford, III ........... A61F 2/2418 |

\* cited by examiner

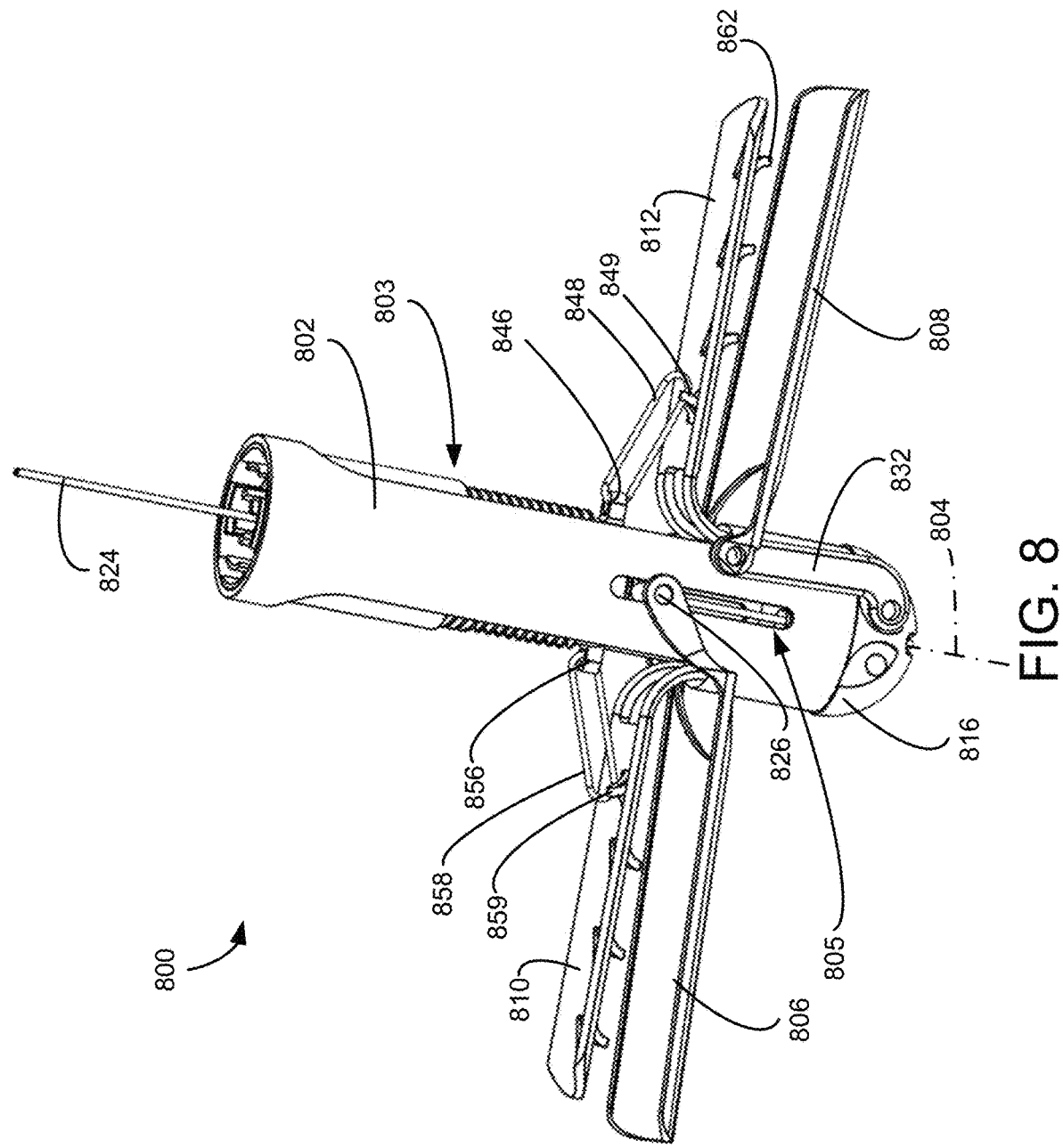

HEART VALVE CLIP

CROSS-REFERENCE TO RELATED APPLICATIONS

This application is related to and claims priority under 35 U.S.C. § 119(e) from U.S. Patent Application No. 63/381,698, filed Oct. 31, 2022, titled "HEART VALVE CLIP", the entire contents of which are incorporated herein by reference for all purposes.

TECHNICAL FIELD

The present disclosure relates generally to medical devices and, in particular, to implantable clips for use in treating heart valve disorders.

BACKGROUND

Mitral regurgitation is a valvular disorder in which blood regurgitates abnormally from the left ventricle into the left atrium during cardiac systole. Left untreated, mitral regurgitation can lead to heart failure, atrial fibrillation, pulmonary hypertension, and even death. Treatment for correcting mitral regurgitation includes implantation of one or more valve clips to reapproximate the anterior and posterior mitral valve leaflets. By reapproximating the leaflets, closure and sealing of the leaflets during ventricular systole can be substantially improved, reducing or even eliminating regurgitation.

Conventional mitral clip procedures have gained substantial popularity and have provided beneficial results to many patients, the procedure is not without complications. For example, removal of conventional mitral clips often requires surgical excision. A relatively high percentage of mitral clip procedures also fail to achieve satisfactory regurgitation reduction or fail to provide long-term results. Although the causes of such issues vary, in at least certain cases, complications arise due to improper or sub-optimal placement and implantation of the mitral clip.

Considering the foregoing, there is a need for valve clips that provide improved control and reliability during implantation, thereby improving results of the implantation process and overall patient outcomes.

SUMMARY

In one aspect of the present disclosure, a valve repair device configured to attach to a native valve of a patient is provided. The valve repair device includes a tubular body defining a longitudinal axis, a paddle supported by the tubular body, and a paddle control mechanism for moving the paddle. The paddle control mechanism includes a paddle collar extending within the tubular body and a paddle shaft extending within the tubular body. The paddle shaft is threadedly engaged to the paddle collar and coupled to the paddle. The paddle collar is rotatable to translate the paddle shaft to change abduction of the paddle relative to the longitudinal axis. The valve repair device further includes a retention member supported by the tubular body proximal the paddle and a retention member control mechanism for moving the retention member to facilitate capture of a valve leaflet between the paddle and the retention member. The retention member control mechanism includes a retention member collar extending within the tubular body and a retention member shaft extending within the tubular body. The retention member shaft is threadedly engaged to the retention member collar and coupled to the retention member. The retention member collar is rotatable to translate the retention member shaft to change abduction of the retention member relative to the longitudinal axis.

In one implementation, the paddle collar and the retention member collar are concentric within the tubular body.

In another implementation, the paddle collar and the retention member collar are concentric within the tubular body and the paddle collar is radially inward of the retention member collar.

In another implementation, rotation of the first collar in a first direction drives the first shaft distally to abduct the paddle relative to the longitudinal axis and rotation of the first collar in a second direction opposite the first direction drives the first shaft proximally to adduct the paddle.

In another implementation, rotation of the second collar in a first direction drives the second shaft distally to abduct the retention member and rotation of the second collar in a second direction opposite the first direction drives the second shaft proximally to adduct the retention member.

In another implementation, the paddle is a first paddle and the valve repair device further includes a second paddle supported by the tubular body. The paddle shaft is further coupled to the second paddle and the paddle collar is rotatable to translate the paddle shaft to simultaneously change each of abduction of the second paddle and abduction of the first paddle relative to the longitudinal axis.

In another implementation, the paddle is a first paddle, the paddle control mechanism is a first paddle control mechanism, the paddle collar is a first paddle collar, and the paddle shaft is a first paddle shaft. The valve repair device further includes a second paddle supported by the tubular body and a second paddle control mechanism for moving the second paddle. The second paddle control mechanism includes a second paddle collar extending within the tubular body and a second paddle shaft extending within the tubular body. The second paddle shaft is threadedly engaged to the second paddle collar and coupled to the second paddle. The second paddle collar is rotatable to translate the second paddle shaft to change abduction of the second paddle relative to the longitudinal axis independent of changing abduction of the first paddle relative to the longitudinal axis.

In another implementation, the retention member is a first retention member and the valve repair device further includes a second retention member supported by the tubular body. The retention member shaft is further coupled to the second retention member and the retention member collar is rotatable to translate the retention member shaft to simultaneously change each of abduction of the second retention member and abduction of the first retention member relative to the longitudinal axis.

In another implementation the retention member is a first retention member, the retention member control mechanism is a first retention member control mechanism, the retention member collar is a first retention member collar, and the retention member shaft is a first retention member shaft. The valve repair device further includes a second retention member supported by the tubular body and a second retention member control mechanism for moving the second retention member. The second retention control mechanism includes a second retention member collar extending within the tubular body and a second retention member shaft extending within the tubular body. The second retention member shaft is threadedly engaged to the second retention member collar and coupled to the second retention member. The second retention member collar is rotatable to selectively translate the second retention member shaft to change abduction of the second paddle relative to the longitudinal axis independent of changing abduction of the first paddle relative to the longitudinal axis.

In another implementation the retention member includes a distal face including a surface feature extending from the distal face and configured to engage the valve leaflet.

In another implementation the retention member is coupled to the retention member shaft by a suture loop.

In another aspect of the present disclosure, another valve repair device is configured to attach to a native valve of a patient is provided. The valve repair device includes a tubular body defining a longitudinal axis, a first paddle supported by the tubular body, a second paddle supported by the tubular body, and a paddle control mechanism for simultaneously changing abduction of the first paddle and the second paddle relative to the longitudinal axis. The valve repair device further includes a first retention member supported by the tubular body proximal the first paddle and a retention member control mechanism for moving the first retention member to facilitate capture of a valve leaflet between the first paddle and the first retention member. The retention member control mechanism includes a retention member collar extending within the tubular body and a retention member shaft extending within the tubular body. The retention member shaft is threadedly engaged to the retention member collar and coupled to the first retention member. The retention member collar is rotatable to selectively translate the retention member shaft to change abduction of the first retention member relative to the longitudinal axis. The valve repair mechanism further includes a second retention member supported by the tubular body proximal the second paddle. The second retention member is movable to change abduction of the second retention member relative to the longitudinal axis.

In one implementation, the second retention member is independently movable from the first retention member.

In another implementation, the retention member control mechanism is a first retention member control mechanism, the retention member collar is a first retention member collar, and the retention member shaft is a first retention member shaft. The valve repair device further includes a second retention member control mechanism for moving the second retention member independently from the first retention member. The second retention control mechanism includes a second retention member collar extending within the tubular body and a second retention member shaft extending within the tubular body. The second retention member shaft is threadedly engaged to the second retention member collar and coupled to the second retention member. The second retention member collar is rotatable to selectively translate the second retention member shaft to change abduction of the second retention member relative to the longitudinal axis. In such implementations, the first retention member may be concentric with the second retention member collar.

In another implementation, the second retention member is movable simultaneously with the first retention member.

In another implementation the retention member shaft is further coupled to the second retention member and the retention member collar is rotatable to translate the retention member shaft to simultaneously change abduction of each of the first retention member and the second retention member relative to the longitudinal axis.

In another aspect of the present disclosure, yet another valve repair device configured to attached to a native valve of a patient is provided. The valve repair device includes a tubular body defining a longitudinal axis, a paddle supported by the tubular body, the paddle movable to change abduction of the paddle relative to the longitudinal axis, and a retention member supported by the tubular body proximal the paddle, the retention member movable to change abduction of the retention member relative to the longitudinal axis. The valve repair device also includes a control mechanism for moving one of the paddle and the retention member. The control mechanism includes a collar extending within the tubular body and a shaft extending within the tubular body, threadedly engaged to the collar, and coupled to one of the paddle and the retention member. The collar is rotatable to translate the shaft to change abduction of the one of the paddle and the retention member relative to the longitudinal axis to facilitate capture of a valve leaflet between the paddle and the retention member.

In one implementation the paddle is a first paddle and the retention member is a first retention member. The valve repair device further includes a second paddle supported by the tubular body and movable to change abduction of the second paddle relative to the longitudinal axis and a second retention member supported by the tubular body proximal the second paddle and movable to change abduction of the second retention member relative to the longitudinal axis.

In another implementation the retention member is biased into abduction.

BRIEF DESCRIPTION OF THE DRAWINGS

The referenced figures of the drawings illustrate various example embodiments of this disclosure. The embodiments and figures described in this disclosure are to be considered illustrative rather than limiting.

FIG. 8 illustrate a valve clip according to one implementation of this disclosure.

DETAILED DESCRIPTION

At least some of the embodiments described herein are directed to devices and methods for repairing a malfunctioning cardiac valve, such as a regurgitant mitral valve. Although many of the examples illustrated and described herein are directed to mitral valve regurgitation, it will be understood that the principles, features, and components described herein may also be applied in other applications, such as repair of other heart valves, or use in other interventional procedures or treatment applications.

Figure 1:
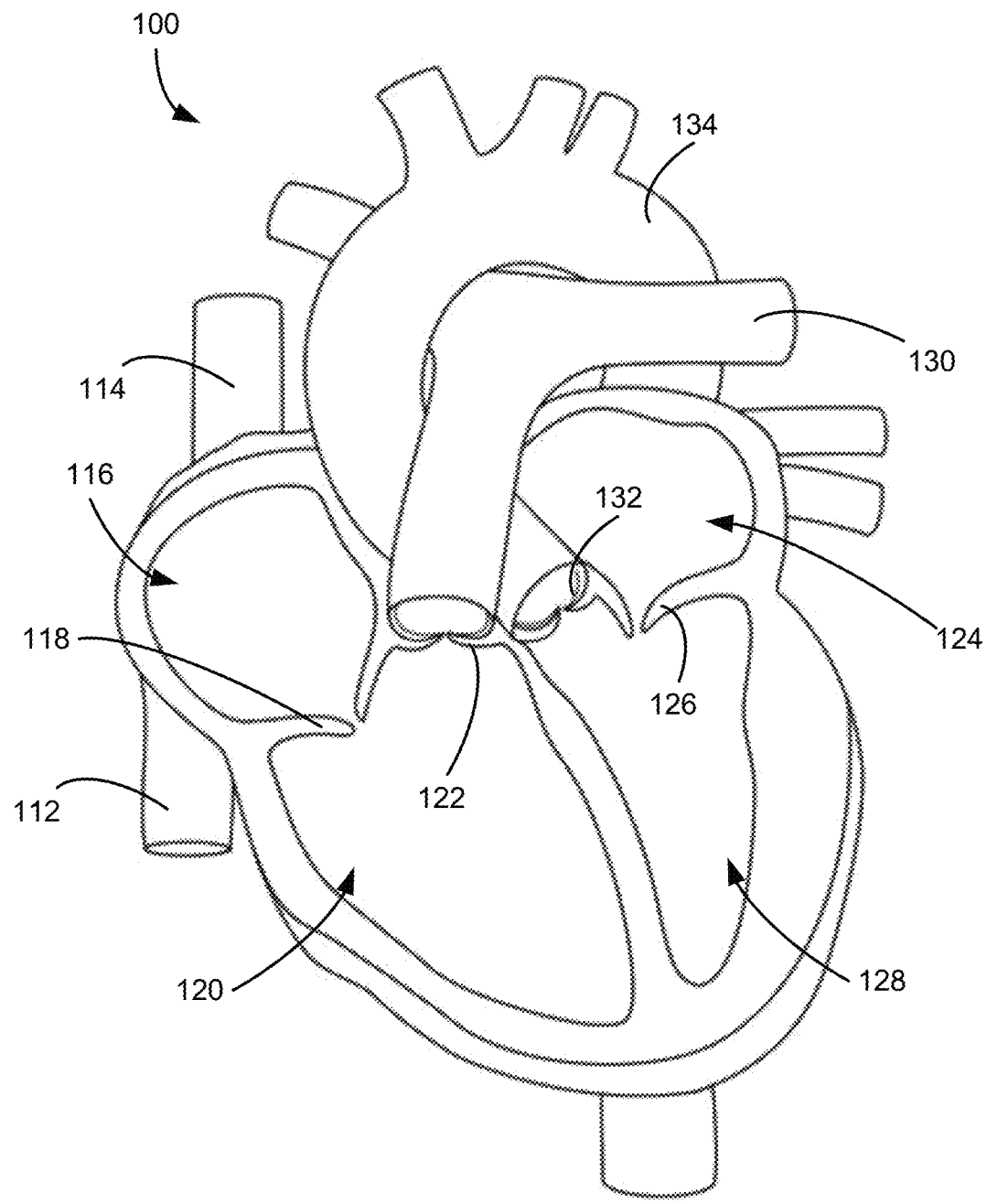
FIG. 1 illustrates a cross-sectional view of a heart.

FIG. 1 illustrates a cross-sectional view of a heart 100. In a normally functioning heart, deoxygenated blood enters the right atrium 116 through the superior vena cava 114 and the inferior vena cava 112. During diastole, the right ventricle 120 expands and the right atrium 116 contracts to create a pressure differential across the tricuspid valve 118, causing blood to flow into the right ventricle 120. During ventricular systole, the right ventricle 120 contracts, forcing blood from the right ventricle 120 through the pulmonary valve 122 and into the pulmonary arteries 130 and to the lungs. Also, during ventricular systole, the tricuspid valve 118 closes to prevent regurgitation of blood from the right ventricle 120 back into the right atrium 116.

Oxygenated blood returning from the lungs enters the left atrium 124. During diastole, contraction of the left atrium 124 and expansion of the left ventricle 128 creates a pressure differential across the mitral valve 126, forcing blood into the left ventricle 128. During ventricular systole, contraction of the left ventricle 128 forces blood through the aortic valve 132 into the aorta 134 for delivery throughout the body. Also, during systole, the mitral valve 126 close to prevent regurgitation of blood from the left ventricle 128 into the left atrium 124.

For various reasons, the tricuspid valve 118 or the mitral valve 126 may be or become pathological and, as a result, may be unable properly seal during systole. In such cases, regurgitation of blood back into the corresponding atrium may occur. Over time, regurgitation can lead to heart failure, atrial fibrillation, pulmonary hypertension, and other issues, up to and including death.

Figure 2:
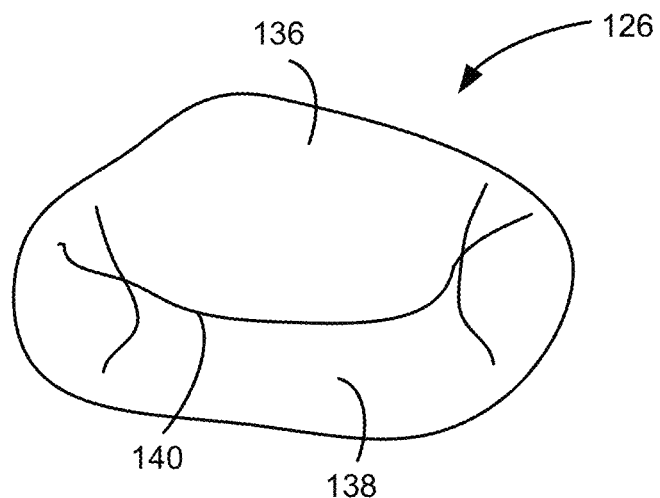
FIG. 2 illustrates a healthy and properly functioning mitral valve in a closed position, e.g., during systole.
Figure 3:
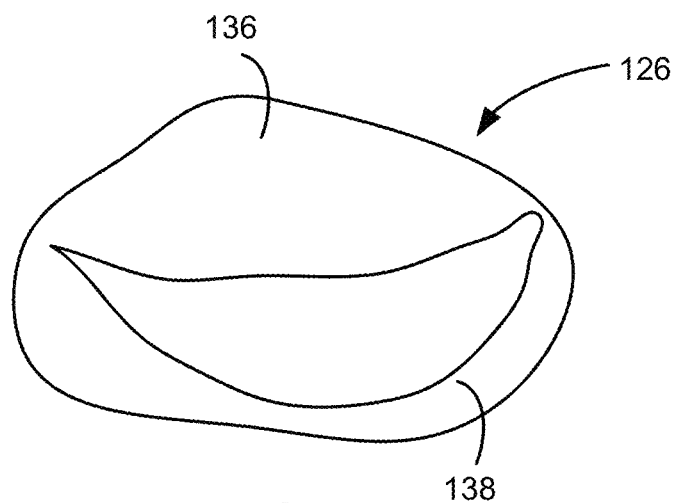
FIG. 3 illustrates a healthy and properly functioning mitral valve in an open position, e.g., during diastole.

FIGS. 2-5 illustrate superior views of the mitral valve 126 in various states and positions. FIG. 2 illustrates a healthy and properly functioning mitral valve 126 in a closed position, e.g., during systole. As shown, the mitral valve 126 includes an anterior leaflet 136 and a posterior leaflet 138 coapt to form a commissure 140, sealing the mitral valve 126 to prevent back flow of blood from the left ventricle 128 into the left atrium 124. In contrast, FIG. 3 illustrates the mitral valve 126 in an open position. When open, the anterior leaflet 136 and the posterior leaflet 138 extend downwardly into the left ventricle 128 to permit blood to flow from the left atrium 124, through the mitral valve 126, and into the ventricle 128.

Figure 4:
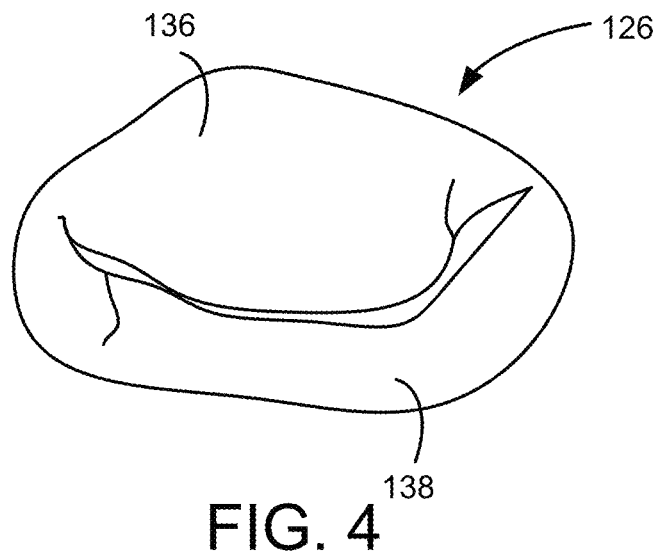
FIG. 4 illustrates a defective mitral valve during ventricular systole.

FIG. 4 illustrates a defective mitral valve 126 during ventricular systole. In contrast to the properly healthy mitral valve of FIG. 2, in which the anterior leaflet 136 and posterior leaflet 138 coapt to form a commissure and seal the left ventricle 128 from left atrium 124, the leaflets of the defective mitral valve do not fully coapt. As a result, no or an incomplete commissure is formed between anterior leaflet 136 and posterior leaflet 138, permitting regurgitant blood to pass through the mitral valve 126 from the left ventricle 128 to left atrium 124. Among other things, the dysfunction of the mitral valve 126 may be due to defects of one or both of the leaflets or defects to other structures of the heart which deform the mitral valve annulus, stretch the chordae tendineae connecting the mitral valve 126 to the surrounding muscle tissue.

Figure 5:
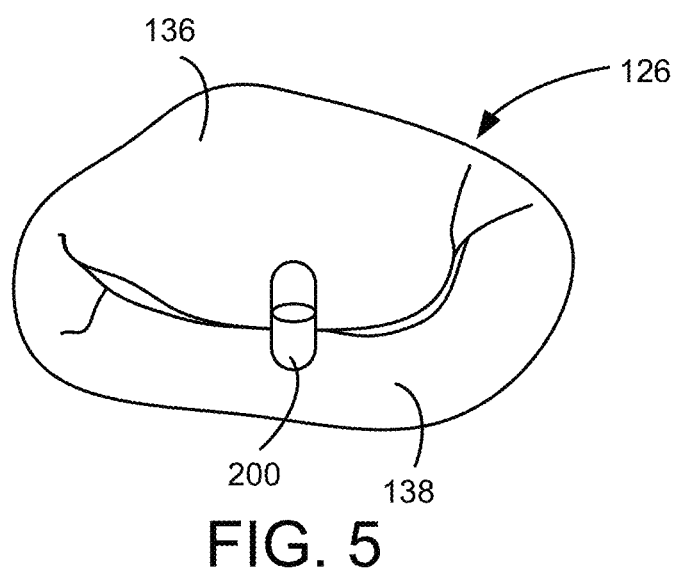
FIG. 5 illustrates a defective mitral valve with a valve clip implanted.

FIG. 5 illustrates a defective mitral valve 126 with a valve clip 200 implanted, i.e., coupled to anterior leaflet 136 and posterior leaflet 138. As illustrated, in at least certain implementations, valve clip 200 may be configured to grip each of the anterior leaflet 136 and the posterior leaflet 138, thereby bringing the two leaflets closer together. By doing so, the travel of the leaflets is reduced, which can enable better coaptation and sealing of the leaflets and general reduction in regurgitation. As illustrated, valve clip 200 is implanted in approximately the middle of mitral valve 126; however, depending on the specific valve dysfunction causing regurgitation, valve clip 200 may be disposed elsewhere between anterior leaflet 136 and posterior leaflet 138 to address mitral clip dysfunctions that may result in no or limited coaptation at other locations.

Figure 6:
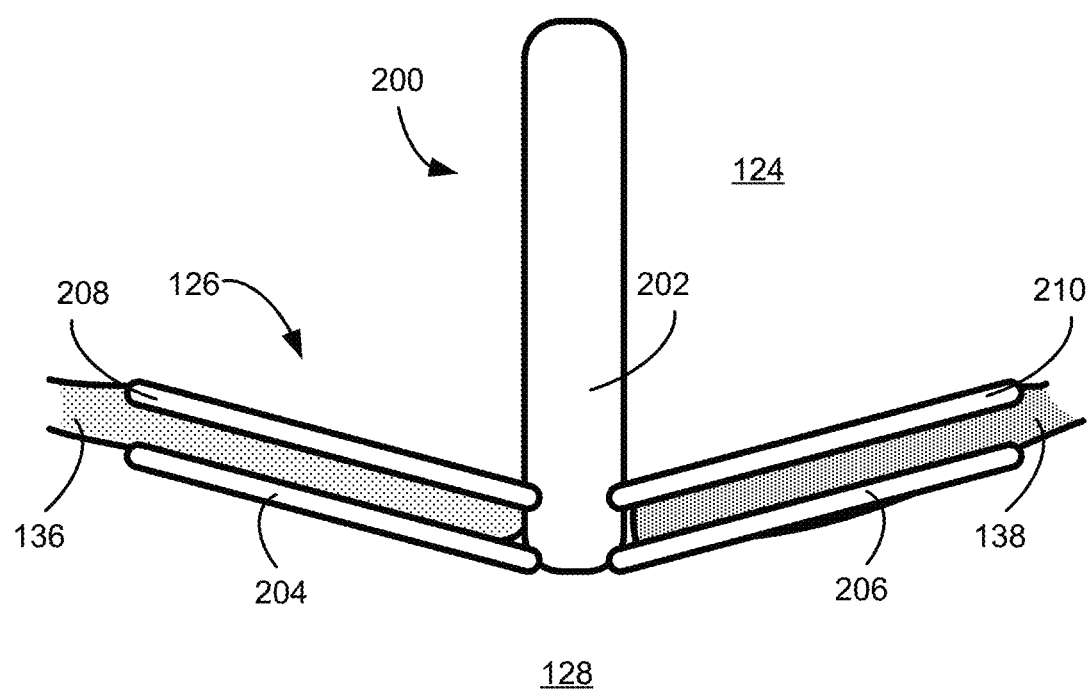
FIG. 6 is a cross-sectional view of the mitral valve with valve clip implanted.

FIG. 6 is a cross-sectional view of the mitral valve 126 with valve clip 200 implanted. As shown, valve clip 200 generally includes a body 202. Valve clip 200 further includes pairs of paddles and retention members between which a respective valve leaflet may be retained. For example, valve clip 200 includes a first paddle 204 and a first retention member 208 disposed proximal the first paddle 204. Valve clip 200 further includes a second paddle 206 and a second retention member 210 disposed proximal the first paddle 204. Each of the paddles and retention members transitions from a closed configuration in which the corresponding component is fully adducted and substantially parallel with body 202 into an open configuration in which a valve leaflet is insertable between each paddle and retention member pair. Following insertion of the valve leaflets, at least a subset of the paddles and retention members is operable to increase gripping force on the leaflet to secure valve clip 200 to the mitral valve 126.

As discussed below in further detail, in certain implementations, the paddles and/or retention members may be operable by an operator (e.g., a physician) to abduct or adduct during implantation. For example, a delivery tool may include a drive mechanism operable by the operator to selectively abduct or adduct one or both paddles. In certain implementations, each paddle may be simultaneously manipulated such that a single drive mechanism may be used to abduct and/or adduct all of the paddles. Alternatively, each paddle may be independently manipulable by a respective drive mechanism. Similarly, a delivery tool may include a drive mechanism operable by an operator to selectively abduct or adduct one or both retention members. In certain implementations, each retention member may be simultaneously manipulated such that a single drive mechanism may be used to abduct and/or adduct all of the retention members. Alternatively, each retention member may be independently manipulable by a respective drive mechanism. In still other implementations, retention members may be optionally biased into abduction. In such implementations, the retention members may or may not be directly driven. In the latter case, the retention members may be manipulated or blocked by contact with and forces applied to the retention members by the corresponding paddles.

FIGS. 7A-7D illustrate a general procedure for implanting valve clip 200 within the heart 100. Beginning in FIG. 7A, an operator navigates a distal end of a delivery tool 700 (e.g., a delivery catheter) into the left atrium 124. Valve clip 200 is releasably coupled to the distal end of delivery tool 700, e.g., using a tether or similar retention mechanism.

Although this disclosure contemplates other delivery techniques, in at least certain implementations, delivery of delivery tool 700 and valve clip 200 into the left atrium 124 may be via a transfemoral route. More specifically, a surgeon may make an incision in the femoral vein in the area of the patient's groin and may subsequently thread a guide wire toward and into the left atrium 124. Following delivery of the guide wire, a delivery catheter may be inserted into the left atrium 124 to provide a delivery pathway for delivery tool 700. In other implementations, delivery tool 700 may be configured to follow the guide wire to the left atrium 124. In such implementations, at least a portion of delivery tool 700 may be sheathed or otherwise covered/protected during delivery. For example, delivery tool 700 may have an exterior movable sheath that is extended over 700, including the distal end of delivery tool 700 with valve clip 200. Following delivery of delivery tool 700 into the left atrium 124, the sheath may be retracted, exposing valve clip 200 and the distal end of delivery tool 700 to facilitate implantation of valve clip 200.

Figure 7A:
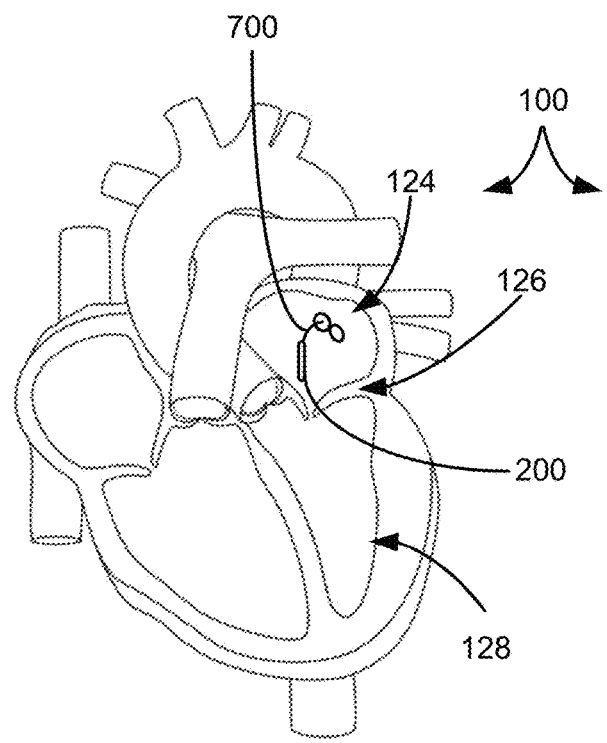
FIGS. 7A-7D illustrate a general procedure for implanting a valve clip within the heart.
Figure 7B:
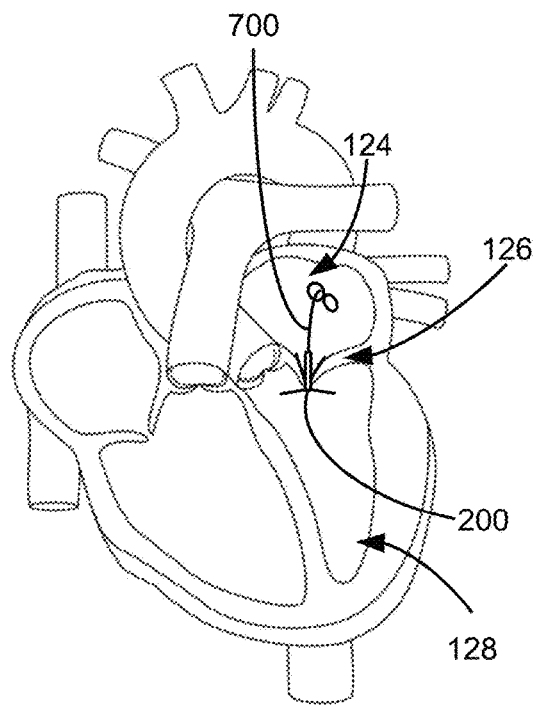

As shown in FIG. 7B, delivery tool 700 is further into heart 100 such that valve clip 200 at least partially crosses the mitral valve 126 into the left ventricle 128. When positioned in this way, valve clip 200 may be deployed in preparation for attaching valve clip 200 to the leaflets of the mitral valve 126. For example, as described below in further detail, deployment of valve clip 200 may include abducting pairs of paddles and retention members in preparation for insertion of the leaflets.

Figure 7C:
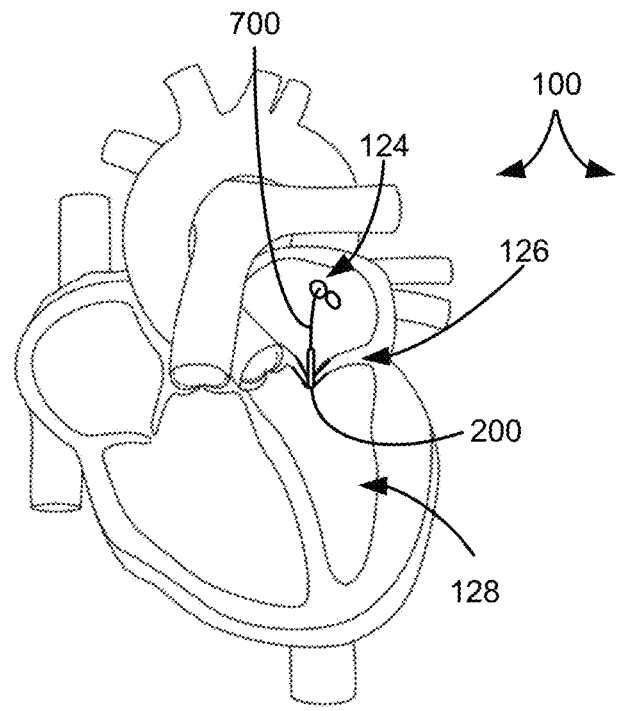
Figure 7D:
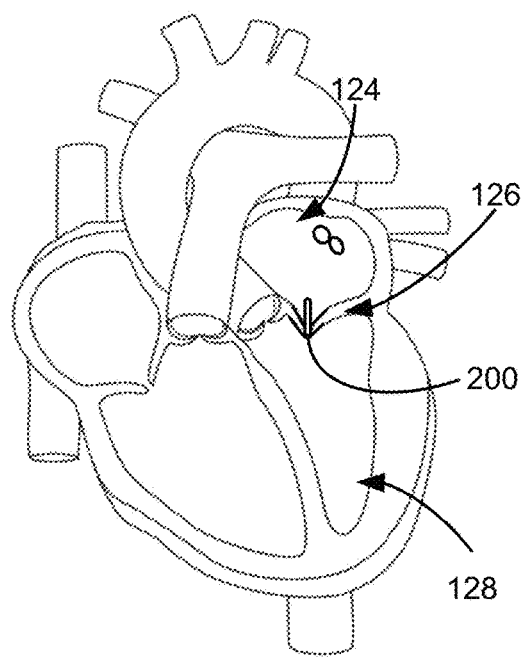

In FIG. 7C, valve clip 200 is manipulated to grip and retain each of anterior leaflet 136 and posterior leaflet 138. As previously noted, valve clip 200 may include paddle and leaflet pairs with each pair configured to receive and retain a valve leaflet. In certain implementations, coupling of the valve clip 200 to the valve leaflets may include performing an initial insertion of each leaflet into a respective paddle and retention member pair and then Finally, in FIG. 7D, valve clip 200 is released from delivery tool 700 and delivery tool 700 is retracted from the heart 100 and the patient; substantially completing the implantation of valve clip 200.

Notably, each of the foregoing steps may be facilitated by fluoroscopy, echocardiography, or similar imaging technology. Accordingly, delivery tool 700 and/or valve clip 200 may be formed, at least in part, from radiopaque, echogenic, or similar materials visible based on the specific imaging (e.g., by including markers, beads, coatings, textiles, or similar elements formed from a radiopaque, echogenic, or other visible material).

Figure 9:
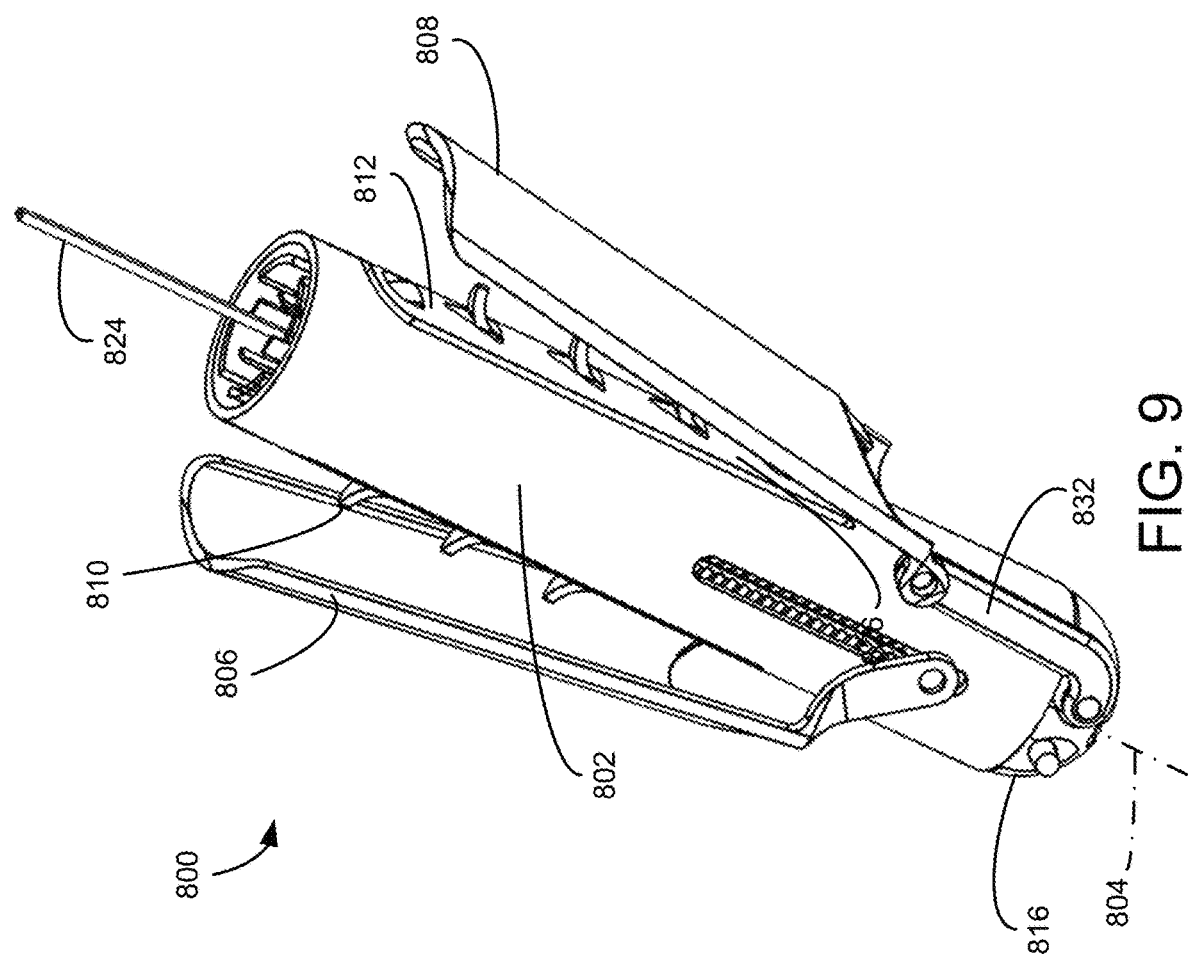
FIG. 9 illustrates the valve clip of FIG. 8 in a partially closed state.
Figure 13:
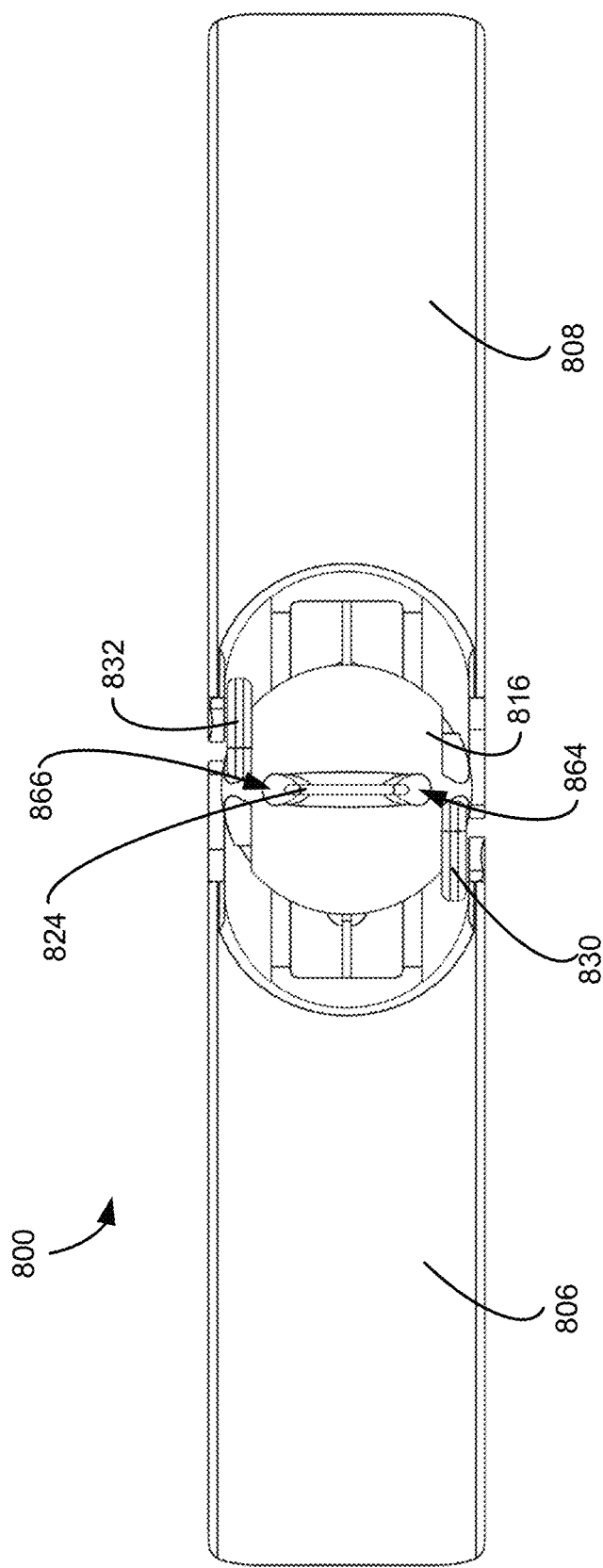
FIG. 13 is a distal view of the valve clip of FIG. 8.
Figure 14:
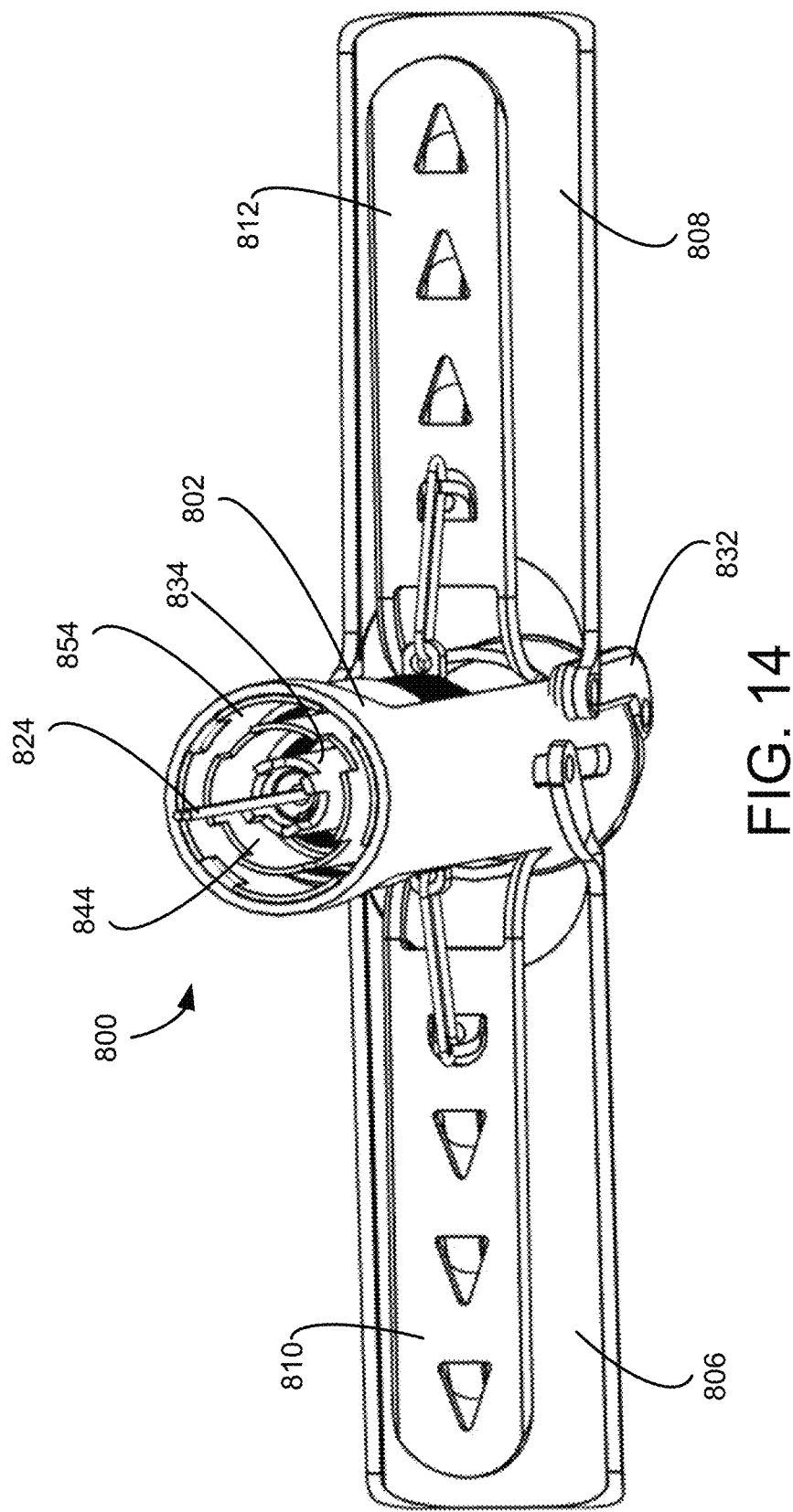
FIG. 14 is a proximal view of the valve clip of FIG. 8 further illustrating the arrangement of various drive mechanisms of the valve clip.
Figure 15:
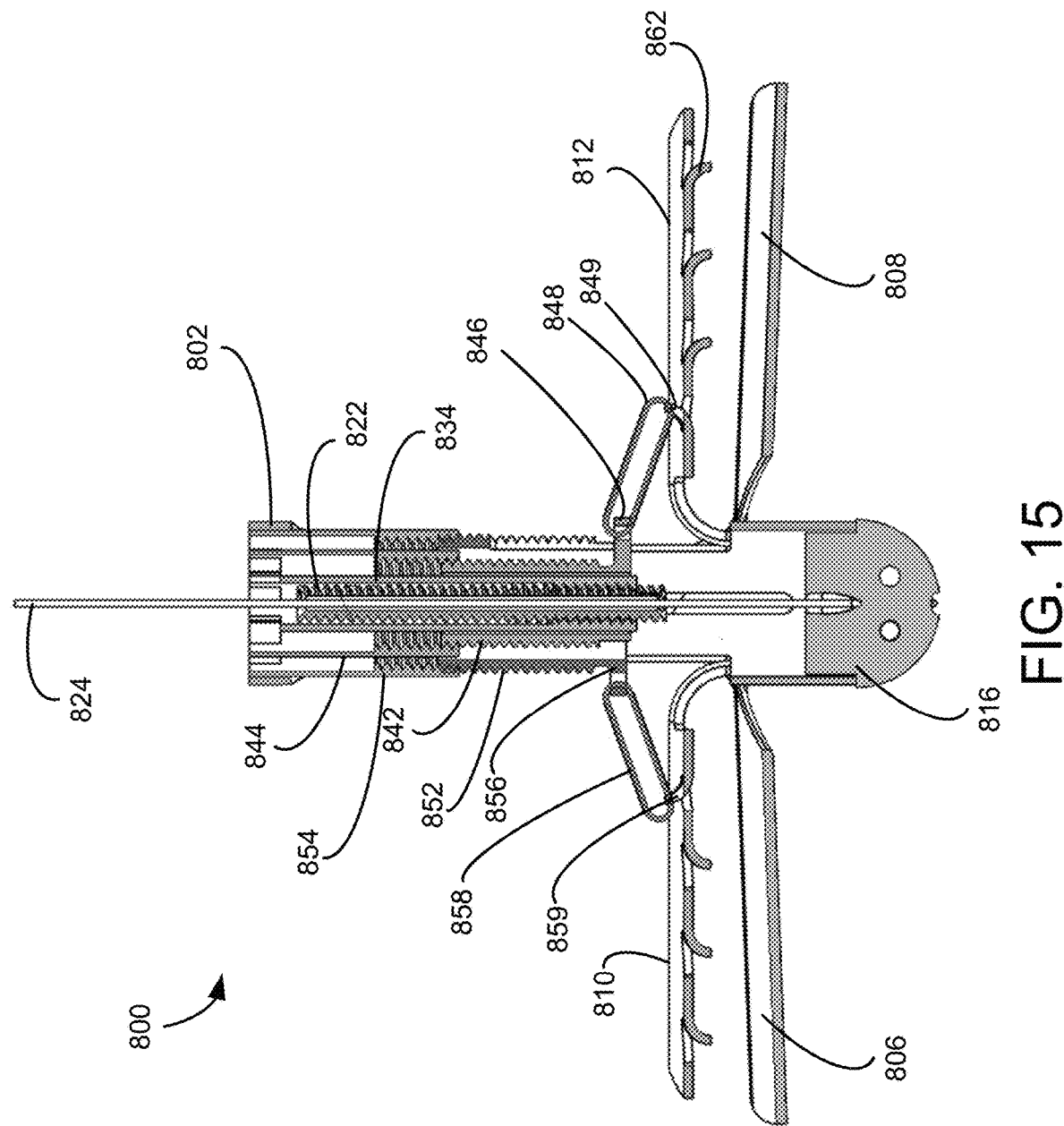
FIG. 15 illustrates a cross-sectional view of the valve clip of FIG. 8.

FIGS. 8-15 illustrate a valve clip 800 according to one implementation of this disclosure. More specifically, FIG. 8 illustrates valve clip 800 in an open state in which valve clip 800 may be placed during placement and implantation. FIG. 9 illustrates valve clip 800 in a partially closed state. FIGS. 10A-14 are further illustrations of valve clip 800 in the open state, each of which is described below in further detail; however, in general FIGS. 10A-14 illustrate valve clip 800 from different perspectives and with components selectively removed to further illustrate internal components and operation of valve clip 800. FIG. 15 is a cross-sectional view further illustrating the relative relationship of the various components discussed in the context of FIGS. 8-14.

Valve clip 800 generally includes a tubular body 802 and defining a longitudinal axis 804 and from which a paddle 806 and a paddle 808 may be selectively extended. Tubular body 802 may terminate in a distal nose 816 disposed along longitudinal axis 804. During delivery of valve clip 800, each of paddle 806 and paddle 808 may be maintained in a closed or undeployed state in which paddle 806 and paddle 808 extend substantially parallel to longitudinal axis 804 along tubular body 802 so valve clip 800 maintains a substantially tubular overall shape. FIG. 9 illustrates valve clip 800 in a partially closed state in which each of paddle 806 and paddle 808 extend close to parallel with longitudinal axis 804. In the fully closed state, each of paddle 806 and paddle 808 extend along/flush with tubular body 802 and substantially parallel to longitudinal axis 804. Following initial delivery of valve clip 800 into the heart (e.g., as illustrated in FIGS. 7A-7D and described above), paddle 806 and paddle 808 may be deployed in preparation for coupling of valve clip 800 with native leaflets of a heart valve.

In general, valve clip 800 is operable to each of abduct and adduct paddle 806 and paddle 808 relative to longitudinal axis 804 during implantation. So, for example, following initial delivery of valve clip 800 into a chamber of the heart (e.g., the left ventricle), an operator may operate valve clip 800 to abduct paddle 806 and paddle 808 from the closed state. Following initial deployment of paddle 806 and paddle 808, the operator may further operate valve clip 800 to selectively abduct or adduct paddle 806 and paddle 808 to facilitate capture and retention of the native valve leaflets. In certain implementations, paddle 806 and paddle 808 may be deployed along a continuum between a fully closed position in which paddle 806 and paddle 808 abut tubular body 802 and extend substantially parallel to longitudinal axis 804 and a fully open position in which paddle 806 and paddle 808 extend at an angle relative to tubular body 802. The maximum angle of paddle 806 and paddle 808 relative to longitudinal axis 804 when paddle 806 and paddle 808 are in the fully open position may vary; however, in at least one implementation, the maximum angle may be up to and including about 120 degrees. More generally, the maximum angle may be up to and including about 135 degrees.

Capture of the native valve leaflets is further facilitated by a retention member 810 and a retention member 812 corresponding to paddle 806 and paddle 808, respectively. As shown in FIG. 8, retention member 810 and retention member 812 are coupled to and extend from tubular body 802 proximal paddle 806 and paddle 808. In certain implementations, retention member 810 and retention member 812 may be integrally formed with tubular body 802. Alternatively, retention member 810 and retention member 812 may be separately formed from but coupled to tubular body 802, e.g., using a pinned or similar joint. Like paddle 806 and paddle 808, retention member 810 and retention member 812 can transition from a closed configuration into an open configuration. For example, in the closed configuration, retention member 810 and retention member 812 extend parallel to longitudinal axis 804 and may be positioned radially inward of paddle 806 and paddle 808 relative to longitudinal axis 804. Accordingly, in at least certain implementations, when paddle 806 and paddle 808 are also in the closed configuration, paddle 806 and paddle 808 may cover retention member 810 and retention member 812. In contrast, when in the open configuration, retention member 810 and retention member 812 may extend outwardly at an angle relative to longitudinal axis 804. In at least one example implementation, when fully open, retention member 810 and retention member 812 may extend at an angle of approximately 90 degrees (e.g., substantially perpendicular) to longitudinal axis 804 when in fully open.

In the implementation illustrated in FIGS. 8-15, paddle 806 and paddle 808 are configured to be simultaneously operable using a paddle control mechanism 820. FIGS. 10A and 10B are illustrations of valve clip 800 with tubular body 802, retention member 810, retention member 812, and associated components removed to better illustrate control mechanism 820. Referring first to FIG. 10A, paddle control mechanism 820 includes a threaded shaft 822 extending longitudinally along longitudinal axis 804. As shown, threaded shaft 822 may be hollow to permit a tether 824 to be threaded through threaded shaft 822 and looped about distal nose 816 to facilitate retention of valve clip 800 on a delivery catheter or similar delivery tool.

Paddle control mechanism 820 further includes a pin 826 and a pin 828 extending laterally from a distal portion of threaded shaft 822. Paddle 806 and paddle 808 are rotatably coupled to pin 826 and 828, respectively, and further coupled to distal nose 816 by respective links. For example, paddle 808 is illustrated in FIG. 10A as being coupled to distal nose 816 by a link 830 and paddle 806 is similarly coupled to distal nose 816 by a link 832.

Figure 10A:
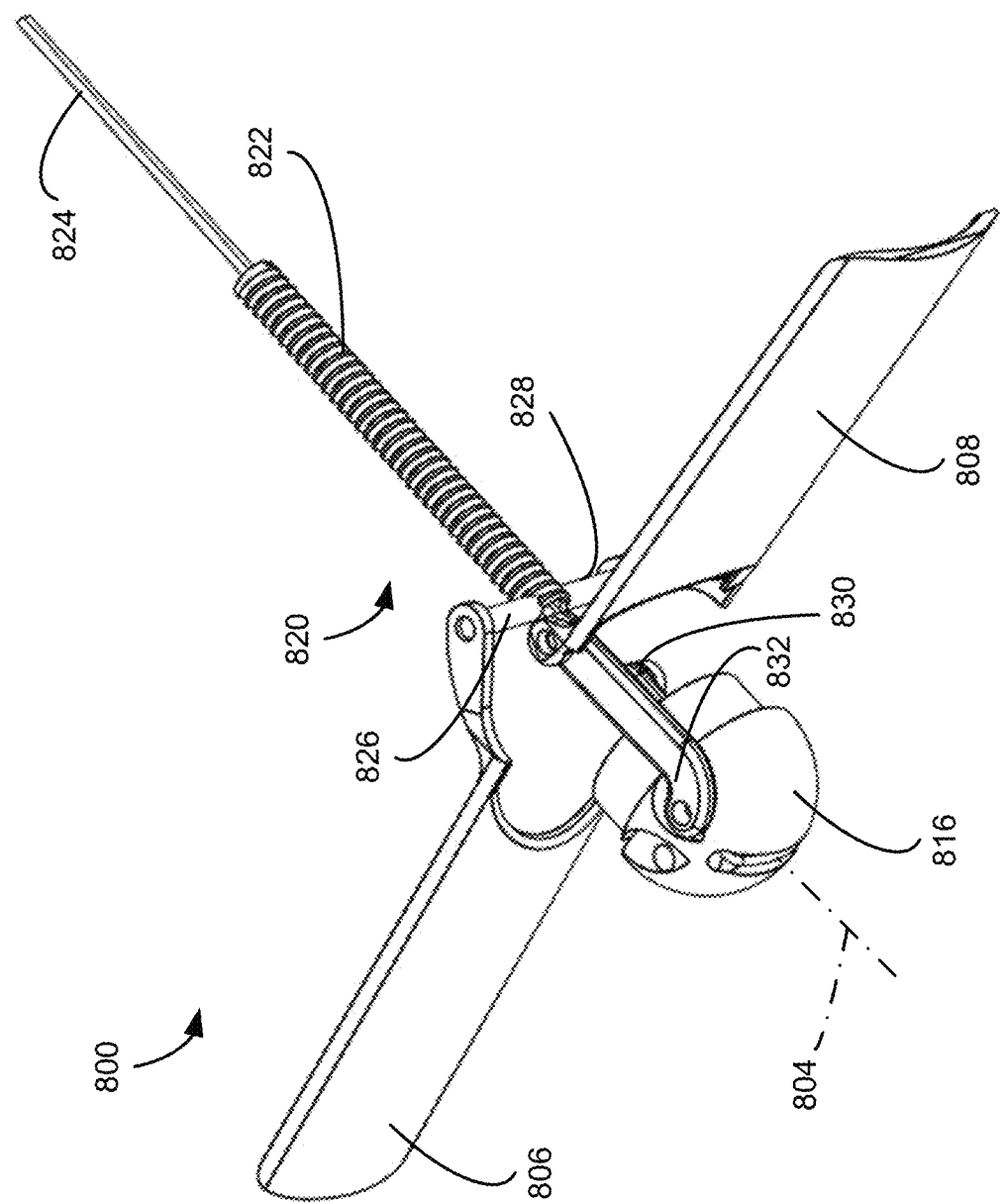
FIGS. 10A and 10B are illustrations of the valve clip of FIG. 8 with various components removed to better illustrate a paddle control mechanism.
Figure 10B:
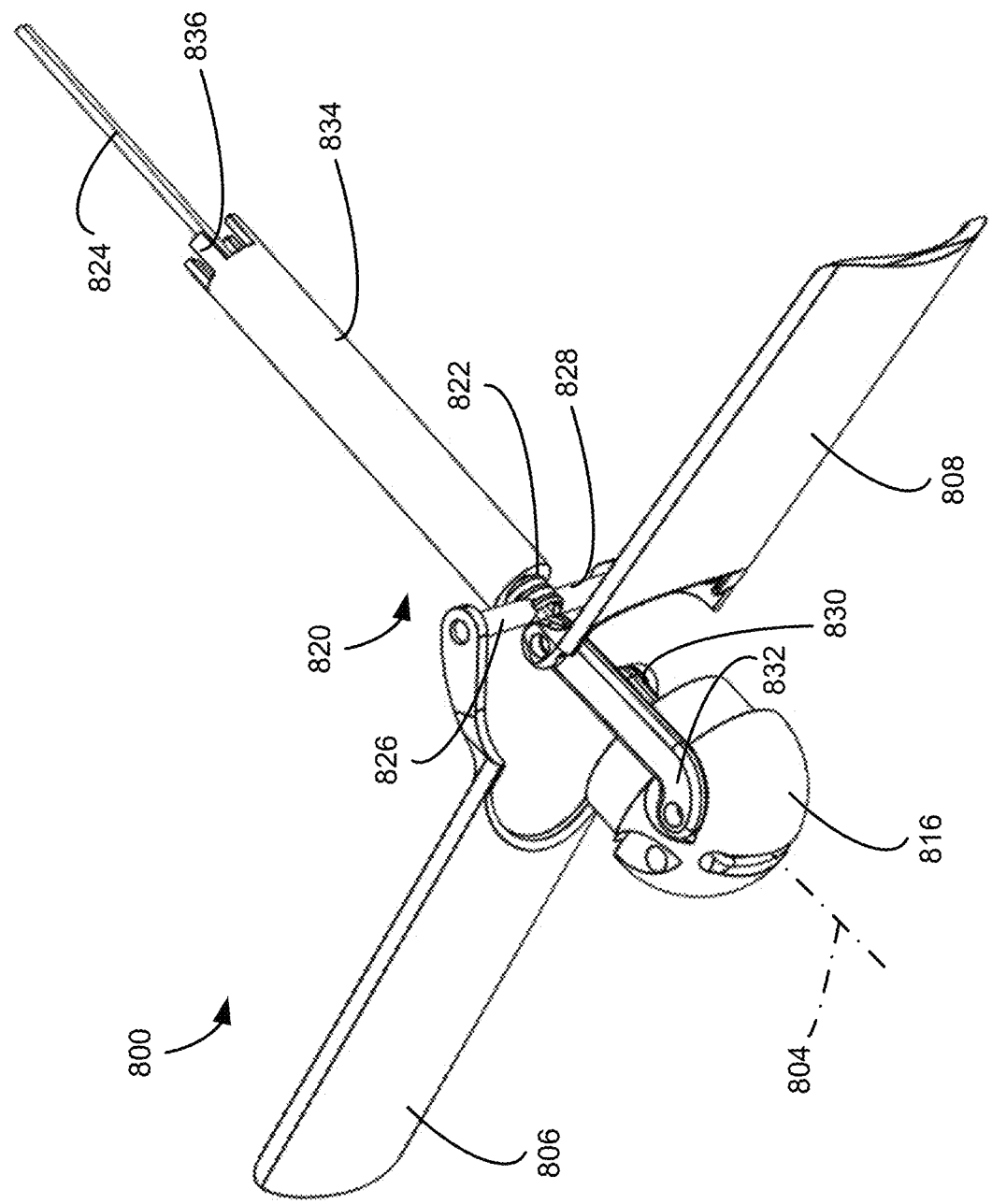

FIG. 10B illustrates substantially the same components of FIG. 10A albeit with the addition of a collar 834 of paddle control mechanism 820. As illustrated, collar 834 is disposed on threaded shaft 822. More specifically, collar 834 includes an internal thread (not shown) that engages the threaded surface of threaded shaft 822.

In general, collar 834 is disposed within tubular body 802 of valve clip 800 such that longitudinal translation of collar 834 is prohibited. For example, tubular body 802 may include shoulders, edges, protrusions, or similar features that retain collar 834 in a longitudinally static position. In contrast, threaded shaft 822 is supported within tubular body 802 but permitted to translate longitudinally at least partially.

Collar 834 includes a proximal engagement feature 836. During operation, a drive tool (not shown) engages proximal engagement feature 836 to facilitate rotation of collar 834. In the specific example of FIG. 10B, proximal engagement feature 836 is in the form of a crenellated distal edge; however, in other implementations proximal engagement feature 836 may have any suitable shape or configuration that permits a tool to mate with and impart a rotational force on collar 834.

Due to the threaded engagement of collar 834 and threaded shaft 822, rotation of collar 834 causes longitudinal translation of threaded shaft 822. For example, in one implementation, rotation of collar 834 in a first direction causes distal translation of threaded shaft 822 while rotation of collar 834 in a second, opposite direction causes proximal translation of threaded shaft 822. Translation of threaded shaft 822 further results in a change in abduction of paddle 806 and paddle 808 relative to longitudinal axis 804 due to the coupling of paddle 806 and paddle 808 to threaded shaft 822 (e.g., by pin 826 and pin 828) and distal nose 816 (e.g., by link 830 and link 832). In the specific example illustrated in FIG. 10B, distal translation of threaded shaft 822 results in adduction of paddle 806 and paddle 808 toward longitudinal axis 804 while proximal translation of threaded shaft 822 results in abduction of paddle 806 and paddle 808 relative to longitudinal axis 804.

Paddle control mechanism 820 is configured to simultaneously drive each of paddle 806 and paddle 808. In other implementations, valve clip 800 may include multiple paddle control mechanisms, each of which may be configured to independently drive one or more paddles. For example, valve clip 800 may be readily modified to include a first paddle drive mechanism for controlling paddle 806 and a second paddle drive mechanism for controlling paddle 808. As further discussed in this disclosure, multiple drive mechanisms may be facilitated by including multiple pairs of concentrically arranged shafts and collars. So, in at least one implementation, a first, inner collar and threaded shaft pair may drive a first paddle while a second, outer collar and threaded shaft pair may drive a second paddle.

Paddle control mechanism 820 is shown in FIGS. 10A and 10B with threaded shaft 822 being outwardly threaded and collar 834 being inwardly threaded. In other implementations, the threading may be reversed with collar 834 being outwardly threaded and threaded shaft 822 being inwardly threaded.

As previously noted, valve clip 800 includes retention member 810 and retention member 812, which may be positioned to facilitate grasping of tissue in conjunction with paddle 806 and paddle 808. More specifically, valve clip 800 may be operated to grasp a first valve leaflet between paddle 806 and retention member 810 and a second valve leaflet between paddle 808 and retention member 812.

With reference to FIG. 8, in certain implementations, each of retention member 810 and retention member 812 transition into an open configuration following positioning of valve clip 800. More specifically, with paddle 806 and paddle 808 positioned on the ventricular side of respective valve leaflets, retention member 810 and retention member 812 abduct relative to longitudinal axis on the atrial side of the leaflets such that the leaflets are positioned between a paddle and retention member.

In certain implementations, retention member 810 and retention member 812 may be biased into abduction. In such implementations, retention member 810 and retention member 812 may be retained by sutures, retractable collars, or similar mechanisms such that, when the mechanism is removed or released, retention member 810 and retention member 812 automatically transition into the open configuration. In other implementations, valve clip 800 may also or alternatively include one or more drive mechanisms for controlling deployment of retention member 810 and retention member 812. In valve clip 800, for example, each of retention member 810 and retention member 812 are biased into an open or abducted configuration; however, valve clip 800 includes separate drive mechanisms for retention member 810 and retention member 812 that permit adduction of retention member 810 and retention member 812 during implantation to facilitate accurate and reliable implantation.

Figure 11:
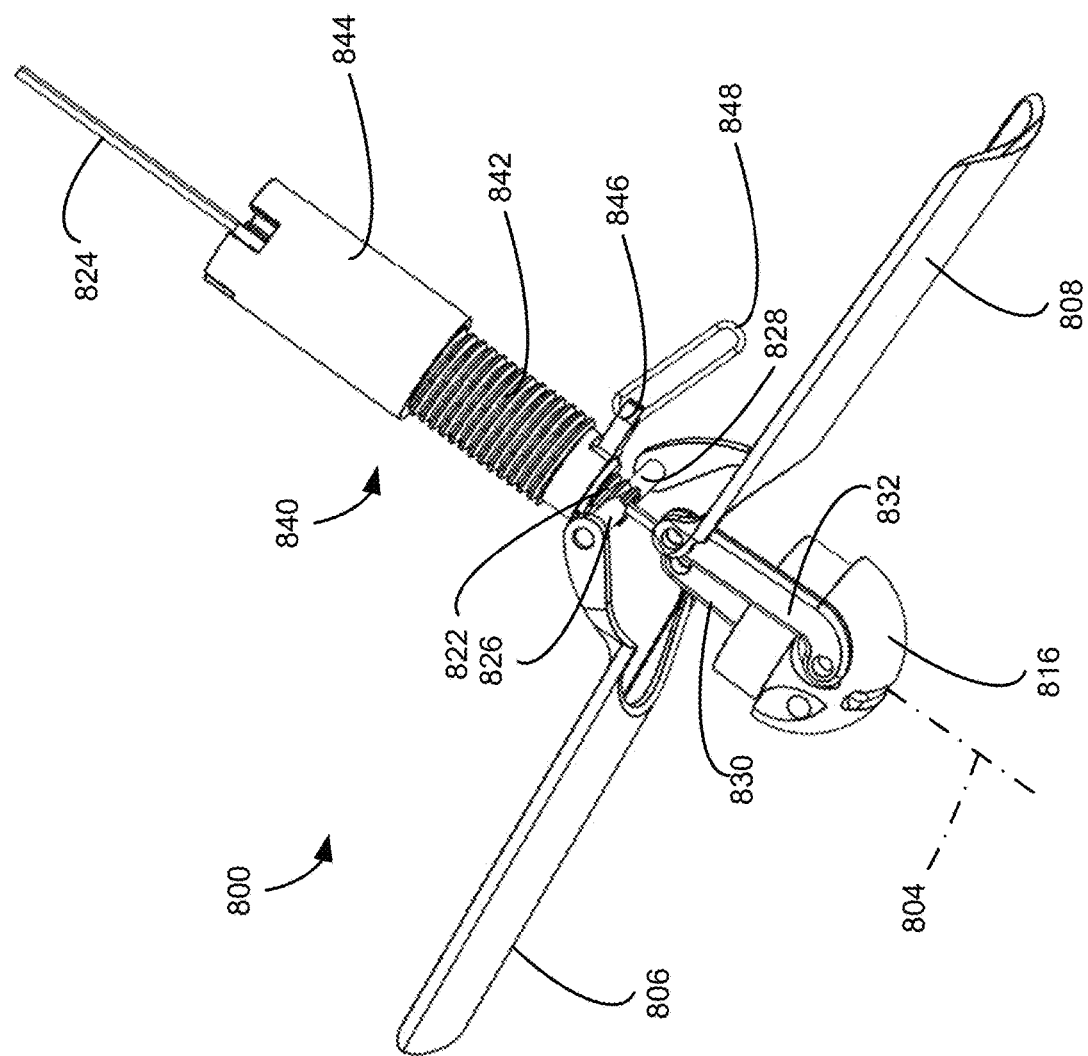
FIG. 11 illustrates a first retention member drive mechanism for a first retention member of the valve clip of FIG. 8.

FIG. 11 illustrates a retention member drive mechanism 840 for retention member 812. Similar to paddle control mechanism 820, retention member drive mechanism 840 includes a threaded shaft 842 and a collar 844. Threaded shaft 842 is illustrated as being externally threaded while collar 844 is internally threaded such that rotation of collar 844 translates threaded shaft 842. Threaded shaft 842 includes a distal tab 846 through which a suture loop 848 extends. As shown in FIG. 8, suture loop 848 is further coupled to a loop 849 extending from a proximal surface of retention member 812. Rotation of collar 844 translates threaded shaft 842 and, as a result, changes tension on suture loop 848. More specifically, as threaded shaft 842 translates proximally, tension on suture loop 848 increases, causing adduction of retention member 812. In contrast, as threaded shaft 842 translates distally, tension on suture loop 848 is released, permitting abduction of retention member 812 due to retention member 812 being biased into abduction.

Figure 12:
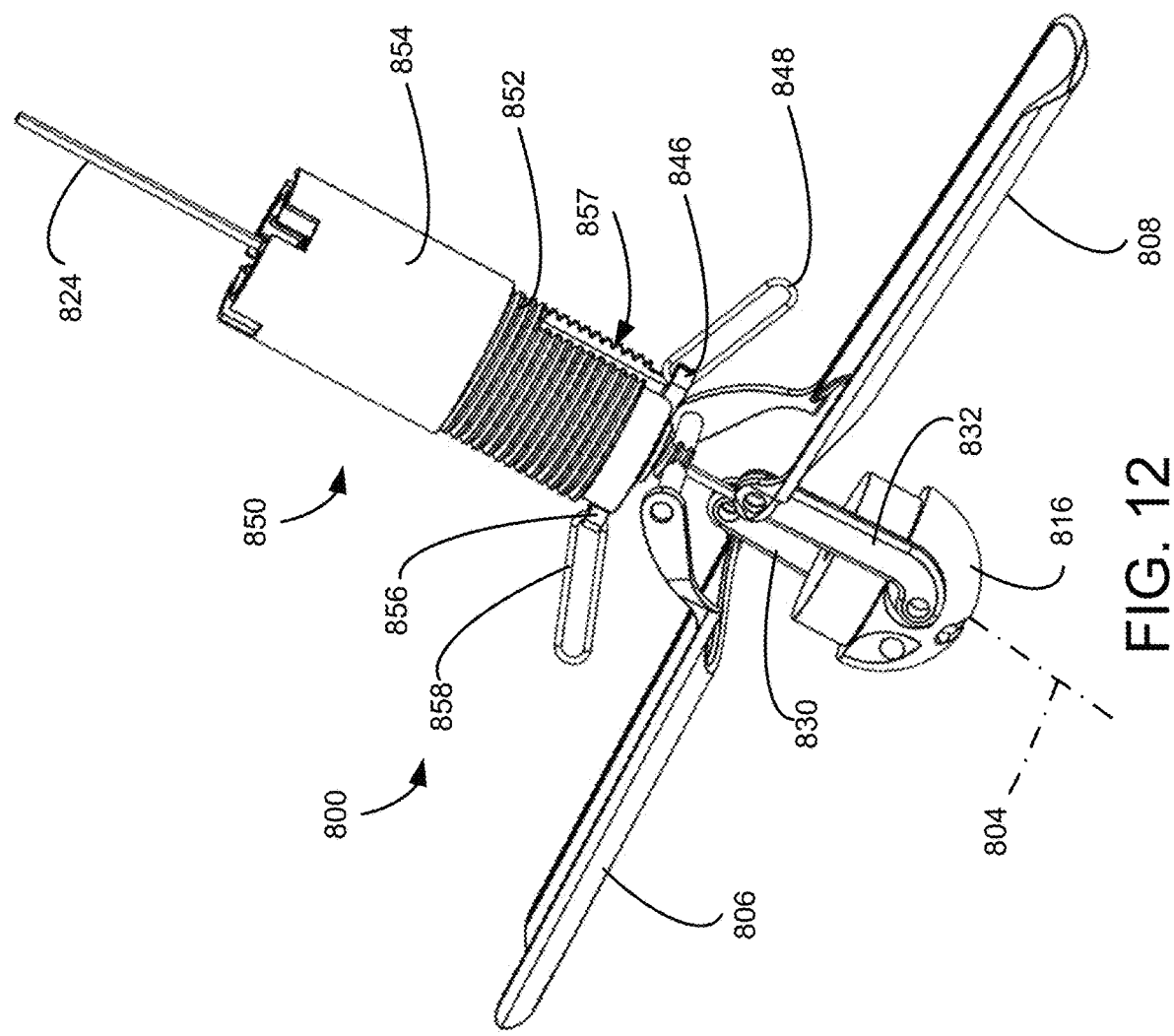
FIG. 12 illustrates a second retention member drive mechanism for a second retention member of the valve clip of FIG. 8.

FIG. 12 illustrates a retention member drive mechanism 850 for retention member 810. Like retention member drive mechanism 840, retention member drive mechanism 850 includes a threaded shaft 852 and a collar 854. Threaded shaft 852 is shown as externally threaded while collar 854 is internally threaded such that rotation of collar 854 translates threaded shaft 852. Threaded shaft 852 includes a distal tab 856 through which a suture loop 858 extends. Referring to FIG. 8, suture loop 858 extends through a loop 859 extending from a proximal surface of retention member 810. Rotation of collar 854 therefore can modify tension on suture loop 858 to change abduction of retention member 810 relative to longitudinal axis 804.

In certain implementations, tubular body 802 may define longitudinal slots, such as longitudinal slot 803, through which the distal tabs of retention member drive mechanism 840 and retention member drive mechanism 850 may extend. More specifically, distal tab 846 of threaded shaft 842 and distal tab 856 of threaded shaft 852 may extend through respective slots formed in tubular body 802 to facilitate coupling of the distal tabs with their respective retention members and translation of the threaded shafts and distal tabs.

Tubular body 802 may also define additional longitudinal slots, such as longitudinal slot 805, through which the pins extending laterally from the distal end of threaded shaft 822 extend. For example, pin 826 of threaded shaft 822 extends through longitudinal slot 805 to couple with paddle 806 and to permit translation of pin 826 during operation of paddle control mechanism 820.

As illustrated in FIGS. 11 and 12, threaded shaft 852 and collar 854 of retention member drive mechanism 850 are disposed radially outward of threaded shaft 842 and collar 844 of retention member drive mechanism 840. To permit longitudinal translation of threaded shaft 842 such that distal tab 846 of threaded shaft 842 can be positioned proximal distal tab 856 of threaded shaft 852, threaded shaft 852 may include a slot 857 or similar structural feature that permits longitudinal travel of distal tab 856.

Referring to FIG. 8, in at least certain implementations, retention member 810 and retention member 812 may include distal surfaces adapted to positively engage cardiac tissue. As shown in FIG. 8, for example, each of retention member 810 and retention member 812 have distal surface features in the form of a laterally extending series of barbs or hooks, such as barb 862 of retention member 812. Accordingly, when a leaflet is gripped between retention member 812 and paddle 808, barb 862 may impinge or penetrate into the leaflet to positively engage the leaflet. Barbs are just one example of a distal surface feature. More generally, the distal face of the retention members may have any suitable shape, treatment, or structural features adapted to improve retention of valve tissue. For example, in certain implementations and as an alternative to barbs or similar structures, the distal faces of the retention members may be roughened or include an adhesive or other high-friction coating, each of which provide improved tissue retention and engagement.

FIG. 13 is a distal view of valve clip 800. As shown in FIG. 13, distal nose 816 may include distal hole 864 and distal hole 866. During delivery, tether 824 may be routed through distal holes 864 and distal holes 866 to form a loop that retains valve clip 800 on a suitable delivery device (not shown). Following implantation, tether 824 may be cut, detached at a proximal end, or otherwise modified to enable pulling of tether 824 and release of valve clip 800.

FIG. 14 is a proximal view of valve clip 800 further illustrating the arrangement of the various drive mechanisms of valve clip 800. More specifically, FIG. 14 illustrates the concentric relationship of paddle control mechanism 820, retention member drive mechanism 840, and retention member drive mechanism 850 with threaded shaft 822 and collar 834 or paddle control mechanism 820 disposed inward of the threaded shafts and collars of retention member drive mechanism 840 and retention member drive mechanism 850. In other implementations, the relative arrangement of the drive mechanisms may be modified. For example, paddle control mechanism 820 may be positioned between or external retention member drive mechanism 840 and retention member drive mechanism 850 with appropriate modification of retention member drive mechanism 840 and retention member drive mechanism 850. For example, in certain implementations slots such as slot 857 (shown in FIG. 12) may be required to enable relative translation between the threaded shafts of the various drive mechanisms.

FIGS. 16-20 illustrate a valve clip 1600 according to another implementation of this disclosure. In contrast to valve clip 800, which included simultaneously movable paddles and independently movable retention members, valve clip 1600 includes independently movable paddles and non-manipulable retention members.

Figure 16:
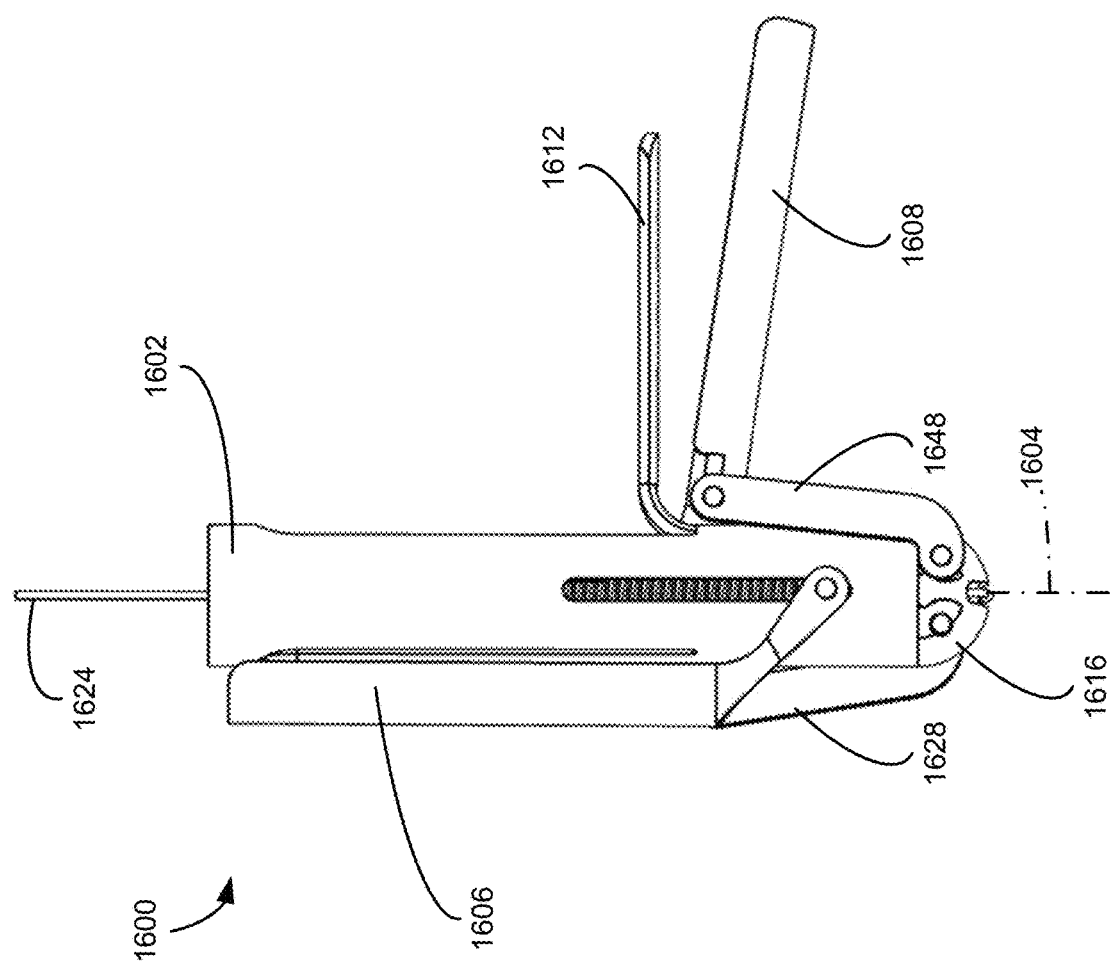
FIG. 16 illustrates a second valve clip according to another implementation of this disclosure.

Referring to FIG. 16, valve clip 1600 generally includes a tubular body 1602 and defining a longitudinal axis 1604 and from which a paddle 1606 and a paddle 1608 may be selectively extended. Tubular body 1602 may terminate in a distal nose 1616 disposed along longitudinal axis 1604. As noted, paddle 1606 and paddle 1608 are independently manipulable in valve clip 1600. To that end, FIG. 16 illustrates valve clip 1600 with paddle 1606 in a fully closed configuration in which paddle 1606 extends substantially parallel to longitudinal axis 1604. In contrast, FIG. 16 shows paddle 1608 in a fully open position in which paddle 1608 is abducted relative to longitudinal axis 1604. In at least certain implementations, paddle 1606 and paddle 1608 may be configured to extend at an angle of up to 135 degrees when fully opened.

While shown in different states in FIG. 16, during delivery of valve clip 1600, each of paddle 1606 and paddle 1608 may be maintained in the closed configuration, i.e., with each of paddle 1606 and paddle 1608 extending substantially parallel to longitudinal axis 1604 along tubular body 1602 so valve clip 1600 maintains a substantially tubular overall shape. Following initial delivery of valve clip 1600 into the heart (e.g., as illustrated in FIGS. 7A-7D and described above), paddle 1606 and paddle 1608 may be deployed in preparation for coupling of valve clip 1600 with native leaflets of a heart valve.

Like paddle 806 and paddle 808 of valve clip 800, in at least certain implementations, paddle 1606 and paddle 1608 may be deployed along a continuum between the fully closed configuration in which paddle 1606 and paddle 1608 abut tubular body 1602 and extend substantially parallel to longitudinal axis 1604 and a fully open position in which paddle 1606 and paddle 1608 extend at an angle relative to tubular body 1602. Further like paddle 806 and paddle 808 of valve clip 800, the maximum angle of paddle 1606 and paddle 1608 relative to longitudinal axis 1604 when paddle 1606 and paddle 1608 are in the fully open position may vary; however, in at least one implementation, the maximum angle may be up to and including about 120 degrees. In another implementation, the maximum angle may be up to and including about 135 degrees. However, in contrast to valve clip 800, valve clip 1600 is operable to each of abduct and adduct paddle 1606 and paddle 1608 relative to longitudinal axis 1604 independent of each other. As a result, valve clip 1600 provides increased flexibility and control of valve clip 1600 during deployment and implantation.

Valve clip 1600 further includes a retention member 1610 (shown in FIG. 20) and a retention member 1612 corresponding to paddle 1606 and paddle 1608, respectively. In valve clip 1600, retention member 1610 and retention member 1612 are passive and valve clip 1600 does not include a mechanism to drive retention member 1610 and retention member 1612. Nevertheless, retention member 1610 and retention member 1612 are configured to be biased into abduction such that as paddle 1606 and paddle 1608 are abducted, retention member 1610 and retention member 1612 may similarly abduct. As illustrated in FIG. 16, retention member 1610 and retention member 1612 may have a maximum abduction less than that of paddle 1606 and paddle 1608 such that when fully opened a gap is present between each paddle and its respective retention member. During implantation, tissue may be inserted into this gap and the corresponding paddle may be adducted to grasp the tissue between the paddle and its retention member. Alternatively, valve clip 1600 may be modified to include drive mechanisms for retention member 1610 and paddle 1608, such as retention member drive mechanism 840 and retention member drive mechanism 850 of valve clip 800. Also, while illustrated in FIGS. 16-20 as having a substantially smooth distal face, retention member 1610 and paddle 1608 may alternatively include barbs, roughening, surface treatments (e.g., coatings) or other similar features to improve engagement and retention of tissue by retention member 1610 and retention member 1612.

In the implementation illustrated in FIGS. 16-20, paddle 1606 and paddle 1608 are independently operable to control their respective abduction relative to longitudinal axis 1604. To facilitate such operation, valve clip 1600 includes a paddle control mechanism 1620 for controlling paddle 1606 and a paddle control mechanism 1640 for separately and independently controlling paddle 1608.

Figure 17:
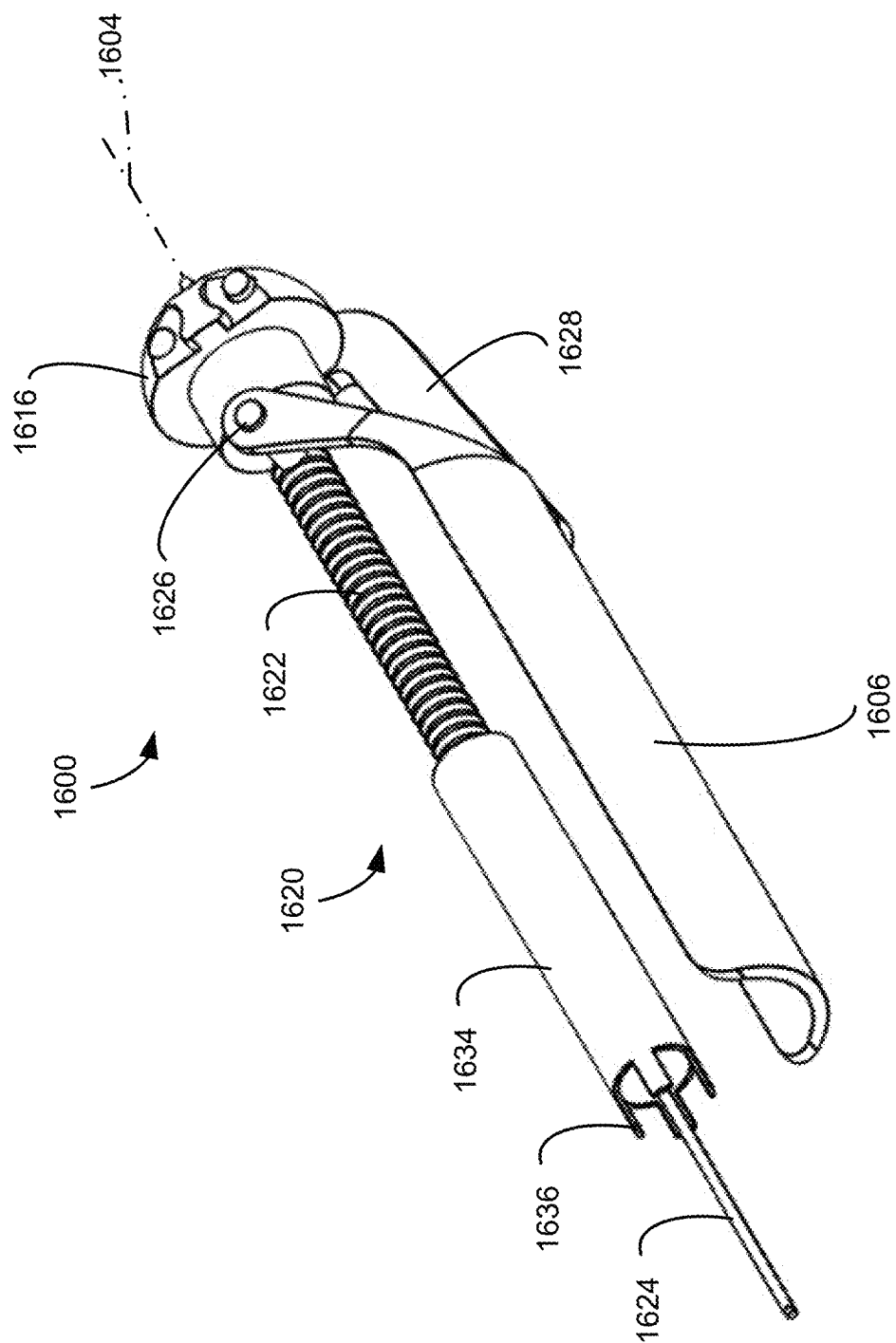
FIGS. 17-19 are illustrations of the valve clip of FIG. 16 with various components removed to better illustrate a paddle control mechanism.

FIG. 17 is an illustration of valve clip 1600 with tubular body 1602, paddle 1608, retention member 1610, retention member 1612, and associated components removed to better illustrate paddle control mechanism 1620. Paddle control mechanism 1620 includes a threaded shaft 1622 extending longitudinally along longitudinal axis 1604. Threaded shaft 1622 may be hollow to permit a tether 1624 to be threaded through threaded shaft 1622 and looped about distal nose 1616 to facilitate retention of valve clip 1600 on a delivery catheter or similar delivery tool.

Paddle control mechanism 1620 further includes a pin 1626 extending laterally from a distal portion of threaded shaft 1622. Paddle 1606 is rotatably coupled to pin 1626 and further coupled to distal nose 1616 by a link 1628. Paddle control mechanism 1620 includes a collar 1634 engaged with threaded shaft 1622. More specifically, collar 1634 includes an internal thread (not shown) that engages the threaded surface of threaded shaft 1622. Collar 1634 is generally disposed within tubular body 1602 of valve clip 1600 such that longitudinal translation of collar 1634 is prohibited. For example, tubular body 1602 may include shoulders, edges, protrusions, or similar features that retain collar 1634 in a longitudinally static position. In contrast, threaded shaft 1622 is supported within tubular body 1602 but permitted to translate longitudinally at least partially.

Collar 1634 includes a proximal engagement feature 1636. During operation, a drive tool (not shown) engages proximal engagement feature 1636 to facilitate rotation of collar 1634. In the specific example of FIG. 17, proximal engagement feature 1636 is in the form of a crenellated distal edge; however, in other implementations proximal engagement feature 1636 may have any suitable shape or configuration that permits a tool to mate with and impart a rotational force on collar 1634.

Due to the threaded engagement of collar 1634 and threaded shaft 1622, rotation of collar 1634 causes longitudinal translation of threaded shaft 1622. For example, in one implementation, rotation of collar 1634 in a first direction causes distal translation of threaded shaft 1622 while rotation of collar 1634 in a second, opposite direction causes proximal translation of threaded shaft 1622. Translation of threaded shaft 1622 further results in a change in abduction of paddle 1606 relative to longitudinal axis 1604 due to the coupling of paddle 1606 to threaded shaft 1622 (e.g., by pin 1626) and distal nose 1616 (e.g., by link 1628). In the specific example illustrated in FIG. 17, distal translation of threaded shaft 1622 results in adduction of paddle 1606 toward longitudinal axis 1604 while proximal translation of threaded shaft 1622 results in abduction of paddle 1606 relative to longitudinal axis 1604.

Figure 18:
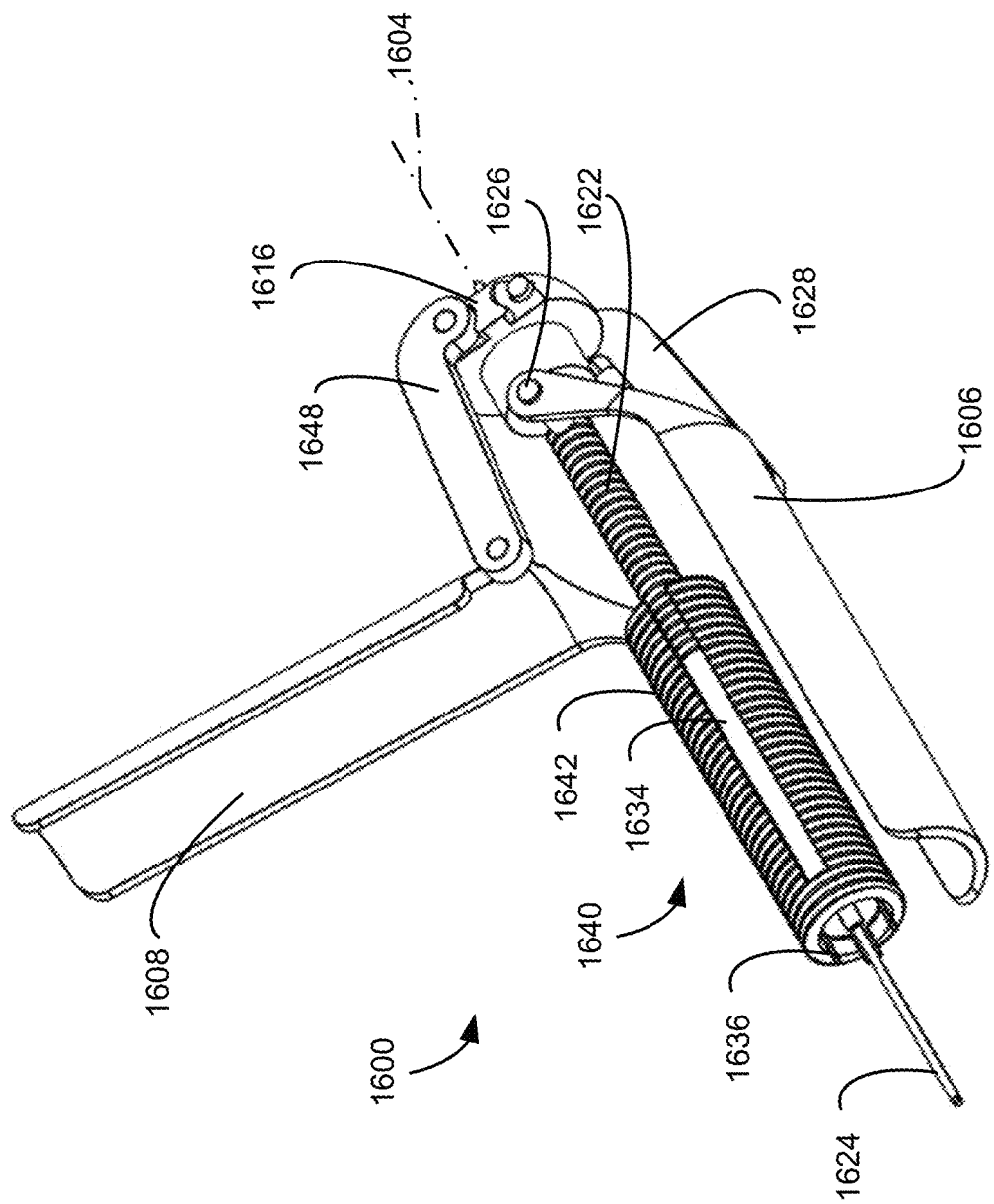
Figure 19:
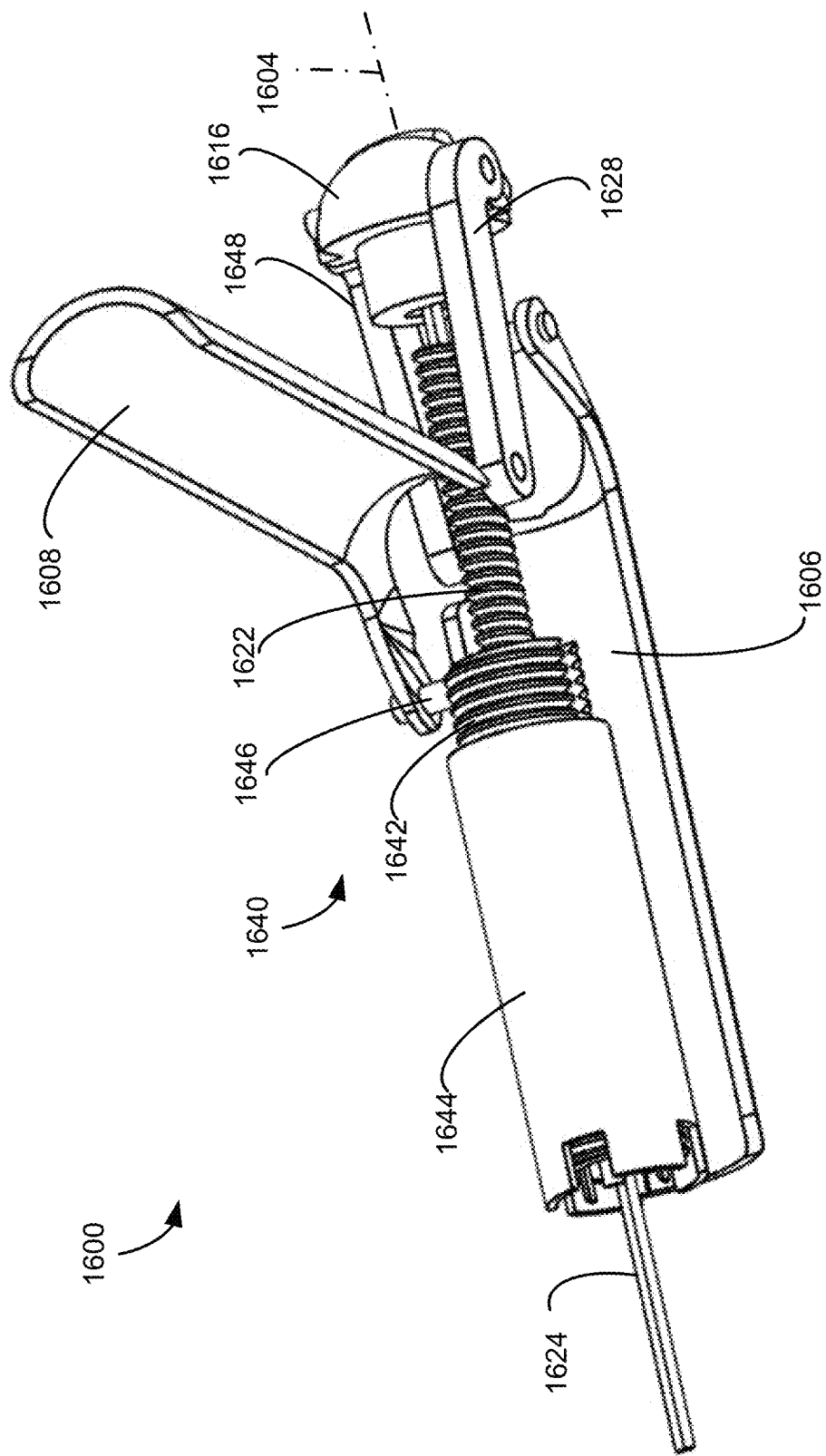

FIGS. 18 and 19 are illustrations of valve clip 1600 with tubular body 1602 and associated components removed to better illustrate paddle control mechanism 1640. Paddle control mechanism 1640 includes a threaded shaft 1642 extending longitudinally along longitudinal axis 1604. Threaded shaft 1642 may be hollow and extend concentrically about threaded shaft 1622 and collar 1634 of paddle control mechanism 1620.

FIG. 18 illustrates paddle control mechanism 1640 with a collar 1644 removed while FIG. 19 includes collar 1644. Like threaded shaft 1622 and collar 1634 of paddle control mechanism 1620, threaded shaft 1642 may include external threads that engage with internal threads of collar 1644 such that rotation of collar 1644 causes translation of threaded shaft 1622. As shown in FIG. 19, a pin 1646 extending laterally from a distal end of threaded shaft 1642 rotatable couples threaded shaft 1642 to paddle 1608. Paddle 1608 is further coupled to distal nose 1616 by a link 1648 (shown most clearly in FIG. 18). Accordingly, as collar 1644 rotates and longitudinally drives threaded shaft 1642, paddle 1608 is made to abduct or adduct relative to longitudinal axis 1604. In the specific implementation shown in FIGS. 18 and 19, rotation of collar 1644 in a first direction causes distal translation of threaded shaft 1642 and adduction of paddle 1608 while rotation in a second, opposite direction causes proximal translation of threaded shaft 1642 and abduction of paddle 1608.

Figure 20:
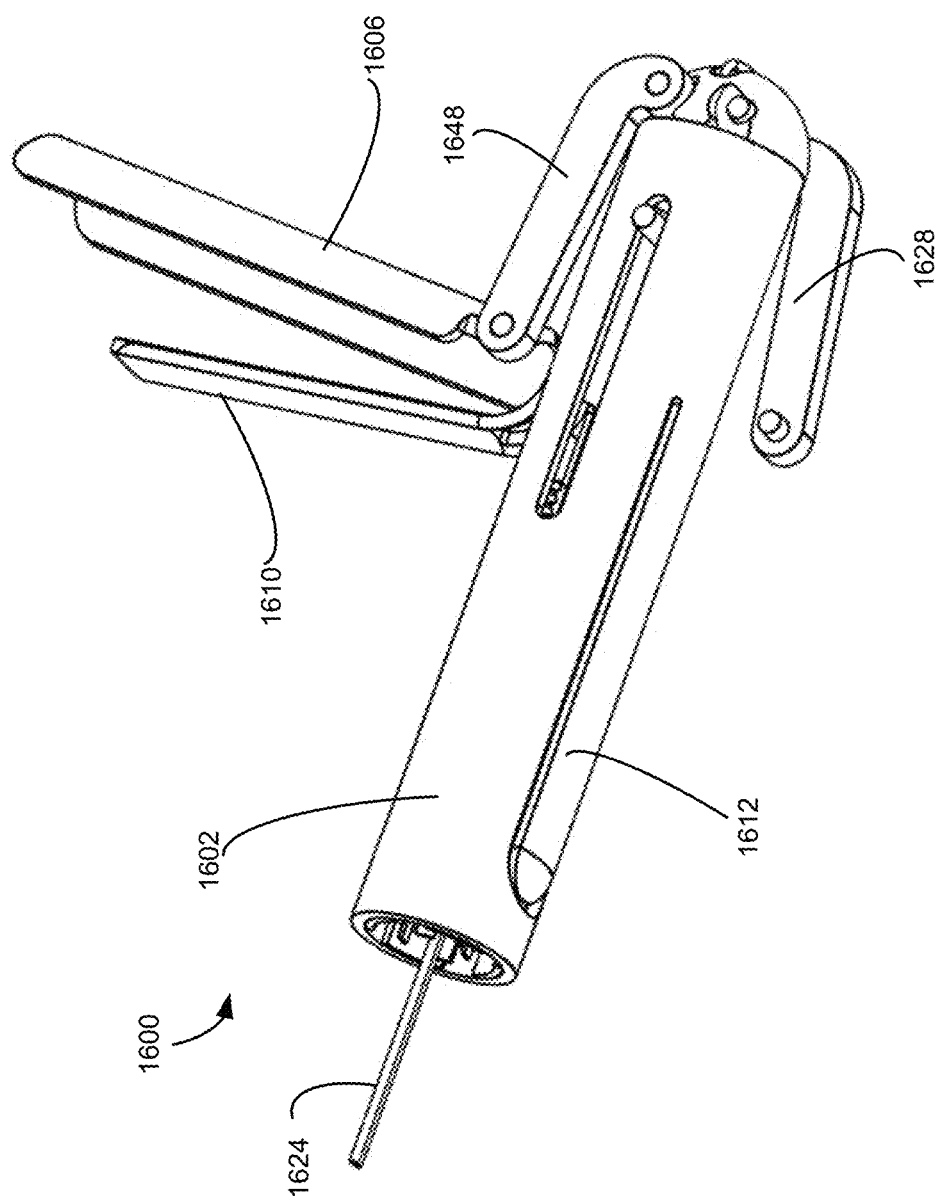
FIG. 20 illustrate the valve clip of FIG. 16 with a paddle removed to illustrate a retention member in a closed position.

As previously discussed, retention member 1610 and retention member 1612 are non-drive in valve clip 1600 and are generally biased into abduction relative to longitudinal axis 1604. FIG. 20 illustrates valve clip 1600 with paddle 1606 hidden to help illustrate this concept. As shown in FIG. 20, retention member 1610 is in a closed or undeployed configuration. In this configuration, retention member 1610 extends along tubular body 1602 and substantially parallel to longitudinal axis 1604. Given that retention member 1610 is biased into abduction, the configuration of retention member 1610 shown in FIG. 20 generally requires that paddle 1606 block or otherwise prevent abduction of retention member 1610. In contrast, paddle 1608 is shown in FIG. 20 in an open or abducted configuration. As a result, retention member 1612 is generally free to abduct due its being biased into abduction.

FIGS. 21-30 illustrate a valve clip 2100 according to another implementation of this disclosure. Like valve clip 800, valve clip 2100 includes simultaneously movable paddles and independently movable retention members.

Figure 21:
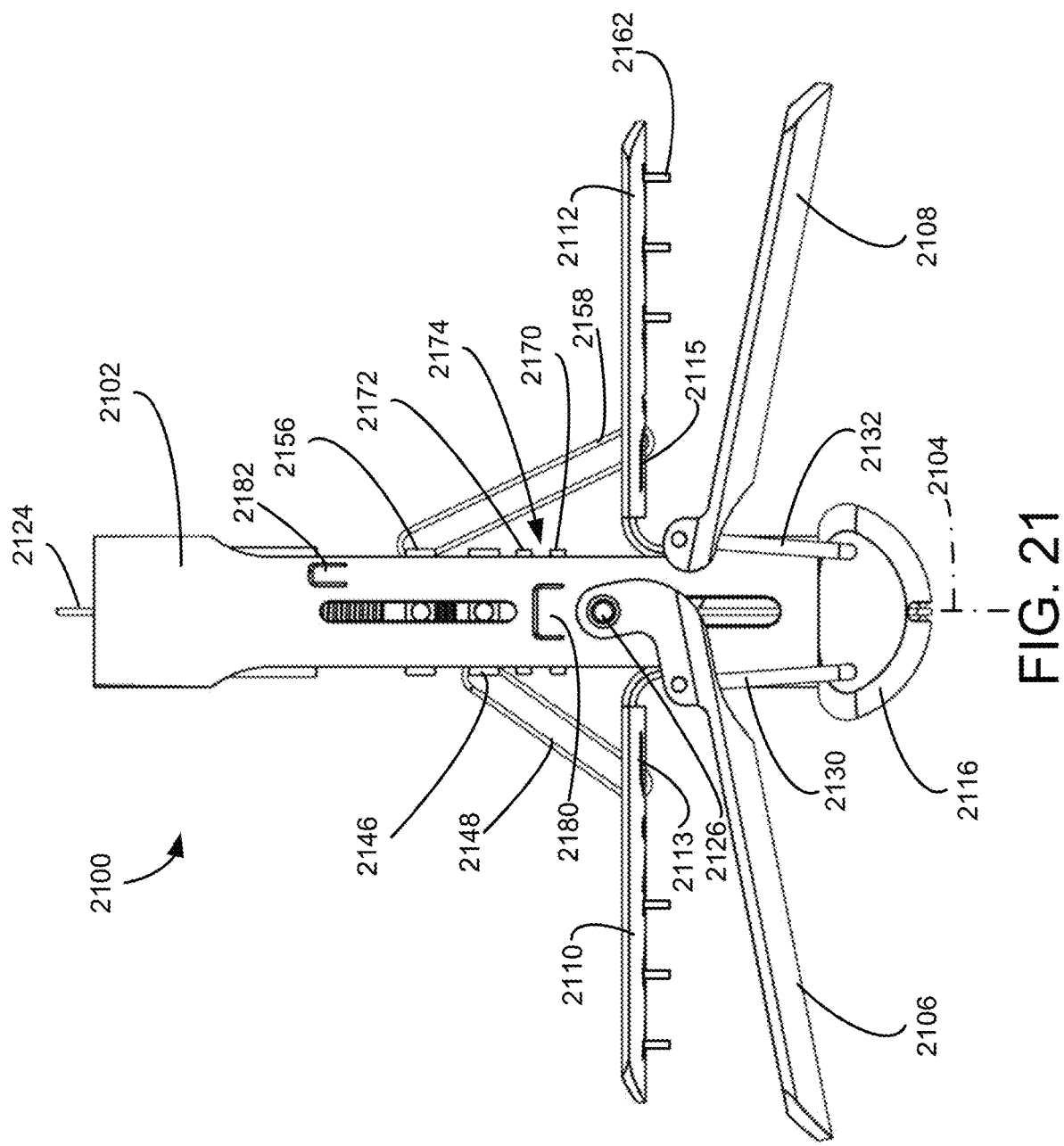
FIG. 21 illustrates a third valve clip according to another implementation of this disclosure and in an open configuration.
Figure 22:
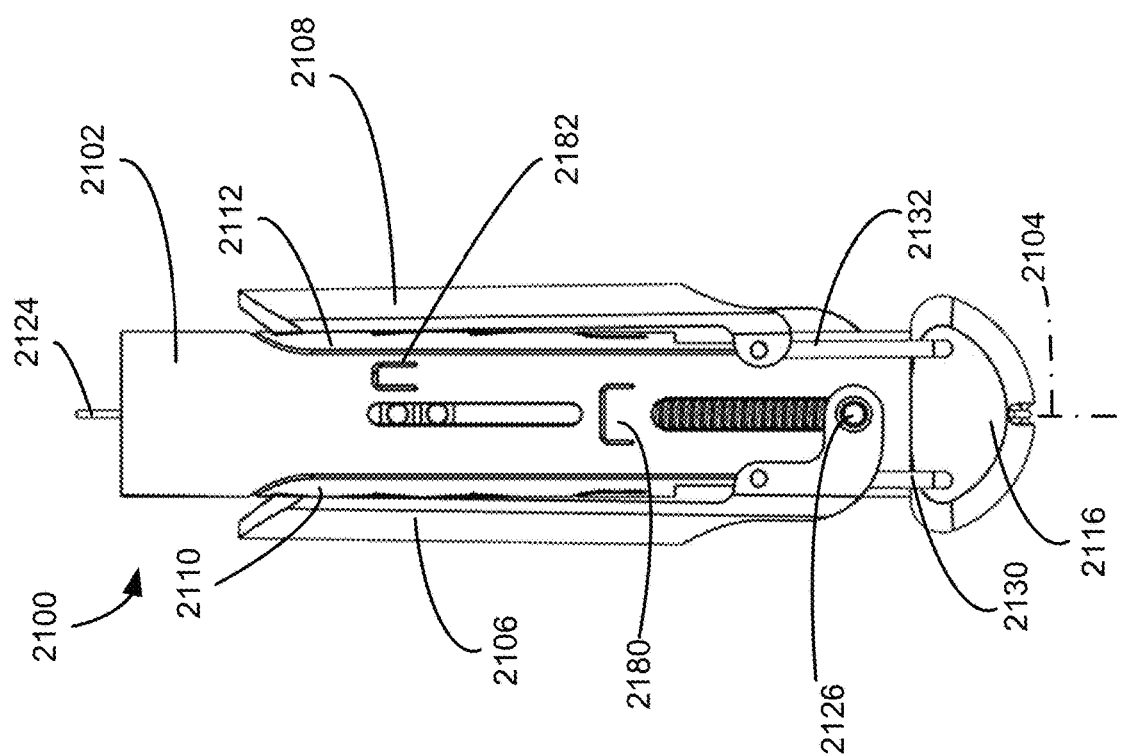
FIG. 22 illustrates the valve clip of FIG. 21 in a closed configuration.

Referring to FIG. 21, valve clip 2100 generally includes a tubular body 2102 and defining a longitudinal axis 2104 and from which a paddle 2106 and a paddle 2108 may be selectively extended. Tubular body 2102 may terminate in a distal nose 2116 disposed along longitudinal axis 2104. As noted, paddle 2106 and paddle 2108 are simultaneously manipulable in valve clip 2100. FIG. 21 illustrates valve clip 2100 with paddle 2106 and paddle 2108 in a fully open configuration while FIG. 17 illustrates valve clip 2100 paddle 2106 and paddle 2108 in a fully closed configuration. In the fully closed configuration, paddle 2106 and paddle 2108 extend substantially parallel to longitudinal axis 2104 and along tubular body 2102. In contrast, FIG. 17 shows paddle 2106 and paddle 2108 in a fully open configuration in which each of paddle 2106 and paddle 2108 are abducted relative to longitudinal axis 2104. In at least certain implementations, paddle 2106 and paddle 2108 may be configured to extend at an angle of up to 135 degrees when fully opened.

During delivery of valve clip 2100, each of paddle 2106 and paddle 2108 may be maintained in the closed configuration shown in FIG. 17, i.e., with each of paddle 2106 and paddle 2108 extending substantially parallel to longitudinal axis 2104 along tubular body 2102 so valve clip 2100 maintains a substantially tubular overall shape. Following initial delivery of valve clip 2100 into the heart (e.g., as illustrated in FIGS. 7A-7D and described above), paddle 2106 and paddle 2108 may be deployed in preparation for coupling of valve clip 2100 with native leaflets of a heart valve.

Like paddle 806 and paddle 808 of valve clip 800, in at least certain implementations, paddle 2106 and paddle 2108 may be deployed along a continuum between the fully closed configuration in which paddle 2106 and paddle 2108 abut tubular body 2102 and extend substantially parallel to longitudinal axis 2104 and a fully open position in which paddle 2106 and paddle 2108 extend at an angle relative to tubular body 2102. Further like paddle 806 and paddle 808 of valve clip 800, the maximum angle of paddle 2106 and paddle 2108 relative to longitudinal axis 2104 when paddle 2106 and paddle 2108 are in the fully open position may vary; however, in at least one implementation, the maximum angle may be up to and including about 120 degrees. In another implementation, the maximum angle may be up to and including about 135 degrees.

Valve clip 2100 further includes a retention member 2110 and a retention member 2112 (each shown in FIG. 21) corresponding to paddle 2106 and paddle 2108, respectively. As described below in further detail, retention member 2110 and retention member 2112 are independently controllable in valve clip 2100. However, retention member 2110 and retention member 2112 may also be biased into abduction such that as paddle 2106 and paddle 2108 are abducted, retention member 2110 and retention member 2112 may similarly abduct, at least in part. As illustrated in FIG. 21, retention member 2110 and retention member 2112 may have a maximum abduction less than that of paddle 2106 and paddle 2108 such that when fully opened a gap is present between each paddle and its respective retention member. During implantation, tissue may be inserted into this gap. Paddle 2106 and paddle 2108 may then be simultaneously adducted to grasp the tissue between each paddle and its corresponding retention member.

Retention members 2110 and paddle 2108 may include barbs, roughening, surface treatments (e.g., coatings) or other similar features to improve engagement and retention of tissue by retention member 2110 and retention member 2112. In the example of valve clip 2100, retention member retention member 2110 and retention member 2112 include barbs (e.g., barb 2162) extending from retention member 2110 and retention member 2112 such that when retention member 2110 and retention member 2112 are in the open configuration, the barbs extend in a substantially distal direction. In at least one specific implementation, the barbs may be formed by making V-shaped (or other shaped) cuts along the length of the retention members and then bending the resulting freed material to form the barbs.

Figure 23:
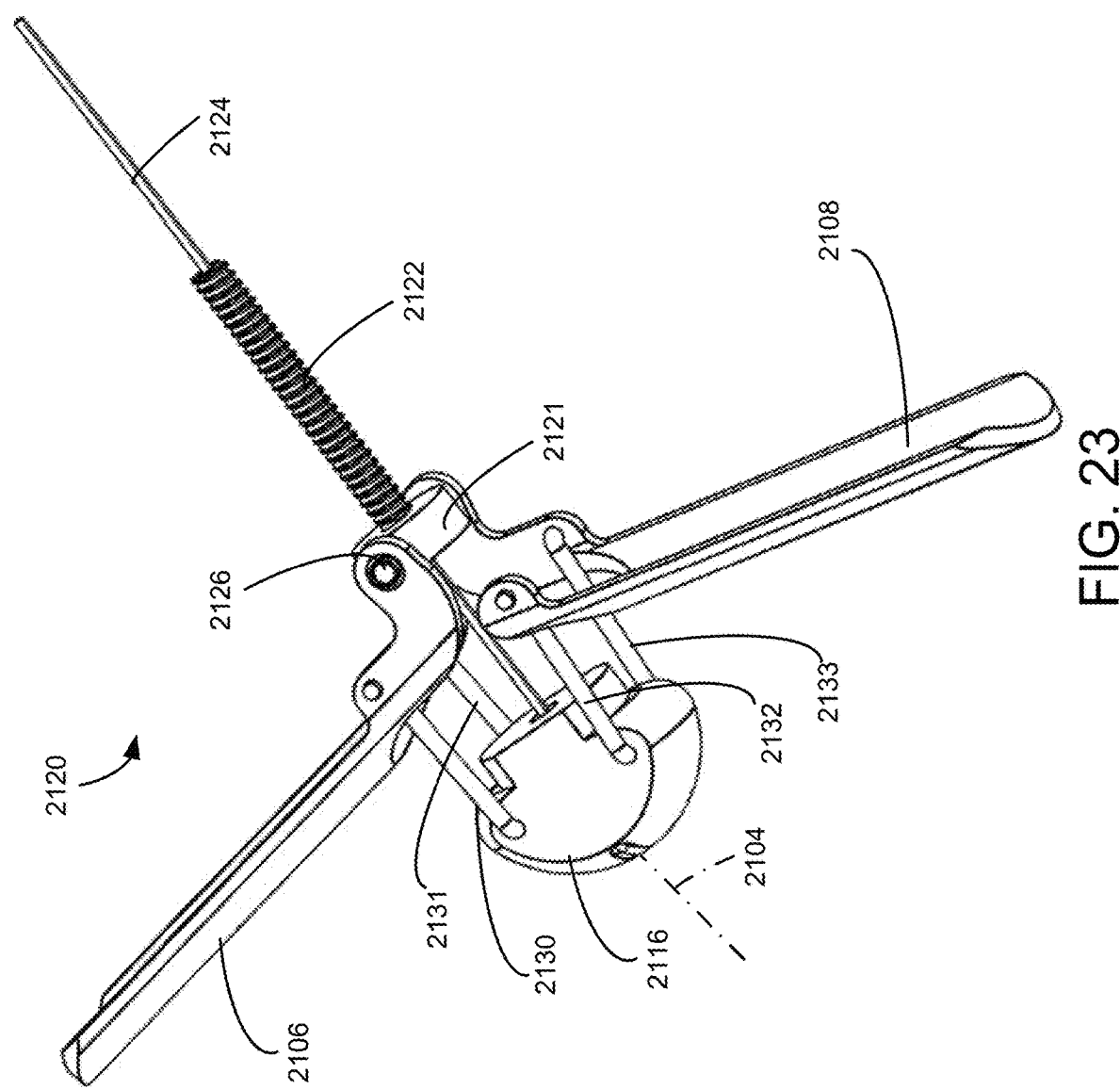
FIGS. 23 and 24 illustrate the valve clip of FIG. 21 with various components removed to better illustrated a paddle control mechanism.

In the implementation illustrated in FIGS. 21-30, paddle 2106 and paddle 2108 are configured to be simultaneously operable using a paddle control mechanism 2120. FIGS. 23-26 are illustrations of valve clip 2100 with tubular body 2102, retention member 2110, retention member 2112, and associated components removed to better illustrate control mechanism 2120. Referring first to FIG. 23, paddle control mechanism 2120 includes a threaded shaft 2122 extending longitudinally along longitudinal axis 2104. As shown, threaded shaft 2122 may be hollow to permit a tether 2124 to be threaded through threaded shaft 2122 and looped about distal nose 2116 to facilitate retention of valve clip 2100 on a delivery catheter or similar delivery tool.

Paddle control mechanism 2120 further includes a pin 2126 and a pin 2128 (obstructed in FIG. 23 but shown in FIG. 29) extending laterally from a distal hub 2121 of threaded shaft 2122. Paddle 2106 and paddle 2108 are rotatably coupled to pin 2126 and pin 2128, respectively, and further coupled to distal nose 2116 by respective pairs of links. For example, paddle 2108 is illustrated in FIG. 23 as being coupled to distal nose 2116 by a link 2130 and a link 2131 and paddle 2106 is similarly coupled to distal nose 2116 by a link 2132 and a link 2133.

Figure 24:
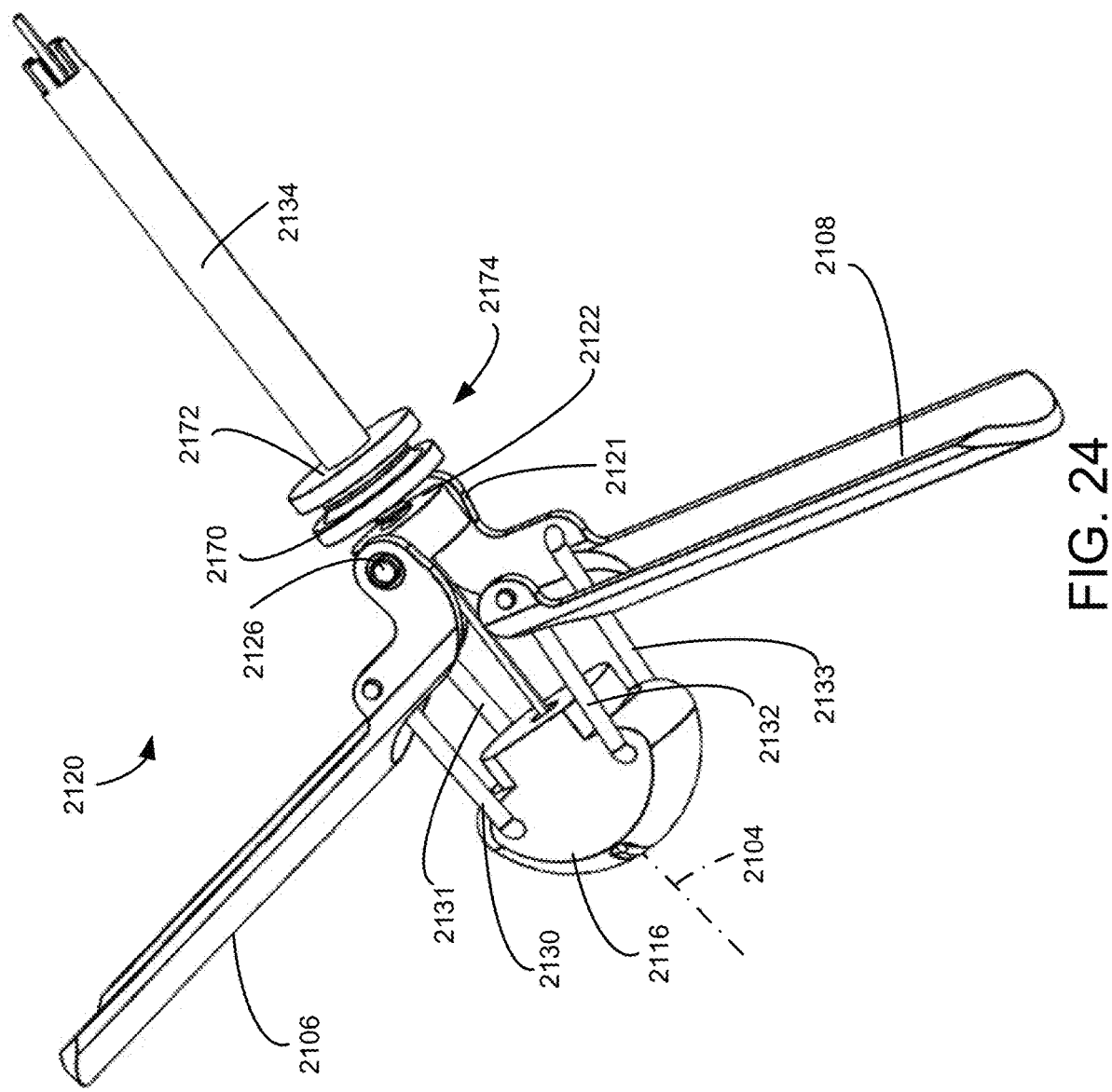

FIG. 24 illustrates substantially the same components of FIG. 23 albeit with the addition of a collar 2134 of paddle control mechanism 2120. As illustrated, collar 2134 is disposed on threaded shaft 2122. More specifically, collar 2134 includes an internal thread (not shown) that engages the threaded surface of threaded shaft 2122.

Collar 2134 is generally configured to be longitudinally retained and to maintain alignment within tubular body 2102. In the specific example of valve clip 2100, collar 2134 includes flanges to facilitate longitudinal retention and alignment. More specifically, collar 2134 includes a distal flange 2170 and a proximal flange 2172 disposed near a distal end of collar 2134 such that distal flange 2170 and proximal flange 2172 define a gap 2174. Distal flange 2170 and proximal flange 2172 have outer diameters that are substantially similar to the inner diameter of tubular body 2102, thereby facilitating alignment of collar 2134 and paddle control mechanism 2120 within tubular body 2102. Also, as discussed below in further detail, when fully assembled, a retention feature (e.g., a bendable tab) of tubular body 2102 may be inserted into gap 2174 to retain and prevent longitudinal travel of collar 2134 and paddle control mechanism 2120 relative to tubular body 2102.

Collar 2134 includes a proximal engagement feature 2136. During operation, a drive tool (not shown) engages proximal engagement feature 2136 to facilitate rotation of collar 2134. In the specific example of FIG. 24, proximal engagement feature 2136 is in the form of a crenellated distal edge; however, in other implementations proximal engagement feature 2136 may have any suitable shape or configuration that permits a tool to mate with and impart a rotational force on collar 2134.

Due to the threaded engagement of collar 2134 and threaded shaft 2122, rotation of collar 2134 causes longitudinal translation of threaded shaft 2122. For example, in one implementation, rotation of collar 2134 in a first direction causes distal translation of threaded shaft 2122 while rotation of collar 2134 in a second, opposite direction causes proximal translation of threaded shaft 2122. Translation of threaded shaft 2122 further results in a change in abduction of paddle 2106 and paddle 2108 relative to longitudinal axis 2104 due to the coupling of paddle 2106 and paddle 2108 to threaded shaft 2122 (e.g., by pin 2126 and pin 2128) and distal nose 2116 (e.g., by link 2130 and link 2131 for paddle 2106 and link 2132 and link 2133 for paddle 2108). In the specific example illustrated in FIG. 24, distal translation of threaded shaft 2122 results in adduction of paddle 2106 and paddle 2108 toward longitudinal axis 2104 while proximal translation of threaded shaft 2122 results in abduction of paddle 2106 and paddle 2108 relative to longitudinal axis 2104.

Paddle control mechanism 820 is configured to simultaneously drive each of paddle 806 and paddle 808. In other implementations, valve clip 800 may include multiple paddle control mechanisms, each of which may be configured to independently drive one or more paddles. For example, valve clip 800 may be readily modified to include a first paddle drive mechanism for controlling paddle 806 and a second paddle drive mechanism for controlling paddle 808. As further discussed in this disclosure, multiple drive mechanisms may be facilitated by including multiple pairs of concentrically arranged shafts and collars. So, in at least one implementation, a first, inner collar and threaded shaft pair may drive a first paddle while a second, outer collar and threaded shaft pair may drive a second paddle.

Figure 25:
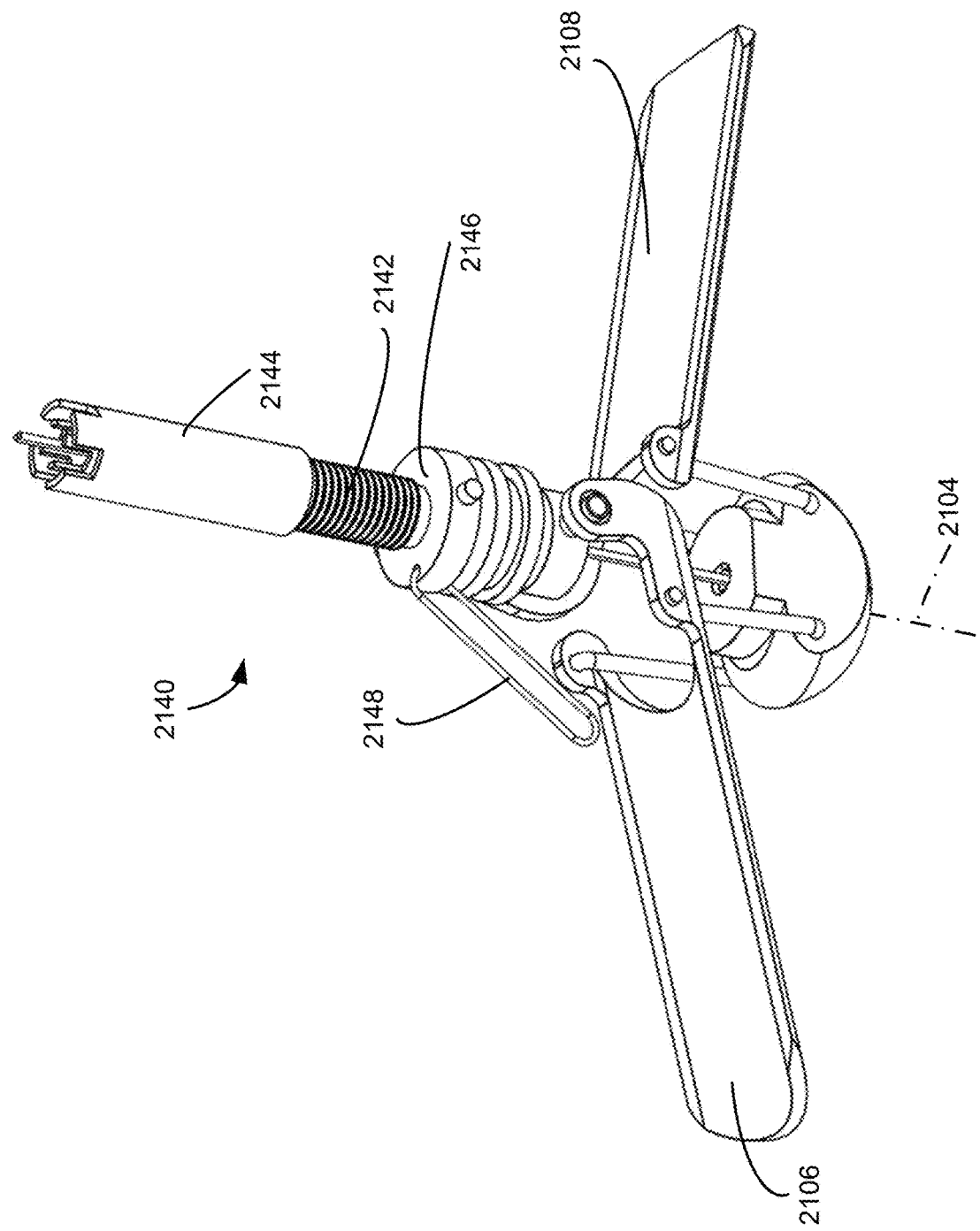
FIG. 25 illustrates the valve clip of FIG. 21 with various components removed to better illustrated a first retention member control mechanism.

FIG. 25 illustrates a retention member drive mechanism 2140 for retention member 2112. For clarity, retention member 2112 is omitted from FIG. 25; however, coupling of retention member 2112 to retention member drive mechanism 2140 is shown in FIG. 21. Similar to paddle control mechanism 2120, retention member drive mechanism 2140 includes a threaded shaft 2142 and a collar 2144. Threaded shaft 2142 is illustrated as being externally threaded while collar 2144 is internally threaded such that rotation of collar 2144 translates threaded shaft 2142. Threaded shaft 2142 includes a distal hub 2146 through which a suture loop 2148 extends. As shown in FIG. 21, suture loop 2148 is looped through corresponding holes defined through retention member 2110. In FIG. 21, for example, retention member 2110 includes a tab 2113 through which suture loop 2148 extends. In certain implementations, tab 2113 may be bent to extend perpendicular (e.g., proximally perpendicular in the arrangement shown in FIG. 21) to retention member 2110. Rotation of collar 2144 translates threaded shaft 2142 and, as a result, changes tension on suture loop 2148. More specifically, as threaded shaft 2142 translates proximally, tension on suture loop 2148 increases, causing adduction of retention member 2112. In contrast, as threaded shaft 2142 translates distally, tension on suture loop 2148 is released, permitting abduction of retention member 2110 due to retention member 2110 being biased into abduction.

Distal hub 2146 may be configured or otherwise include features to facilitate alignment and prevent rotation of threaded shaft 2142 during operation. For example, distal hub 2146 generally has an outer diameter that corresponds to the inner diameter of tubular body 2102, facilitating alignment of retention member drive mechanism 2140 and threaded shaft 2142 within tubular body 2102. Distal hub 2146 further includes one or more protrusions shaped to be received within corresponding longitudinal slots defined by tubular body 2102. For example, distal hub 2146 includes a first protrusion 2145 and a second protrusion 2147 (obstructed in FIG. 25 but shown in FIG. 29) that are respectively received within a first slot 2149 (shown in FIGS. 21 and 27) and a second slot 2151 (shown in FIG. 29) formed in tubular body 2102. During operation and, more specifically, during rotation of collar 2144, the slots of tubular body 2102 prevent rotation of threaded shaft 2142 due to interference with the protrusions of distal hub 2146 while still permitting longitudinal travel of threaded shaft 2142. In certain implementations, the protrusions extending from distal hub 2146 may be integrally formed with distal hub 2146 or may be attached to a surface of distal hub 2146. In other implementations, the protrusions may be pins or similar components inserted into distal hub 2146.

Figure 26:
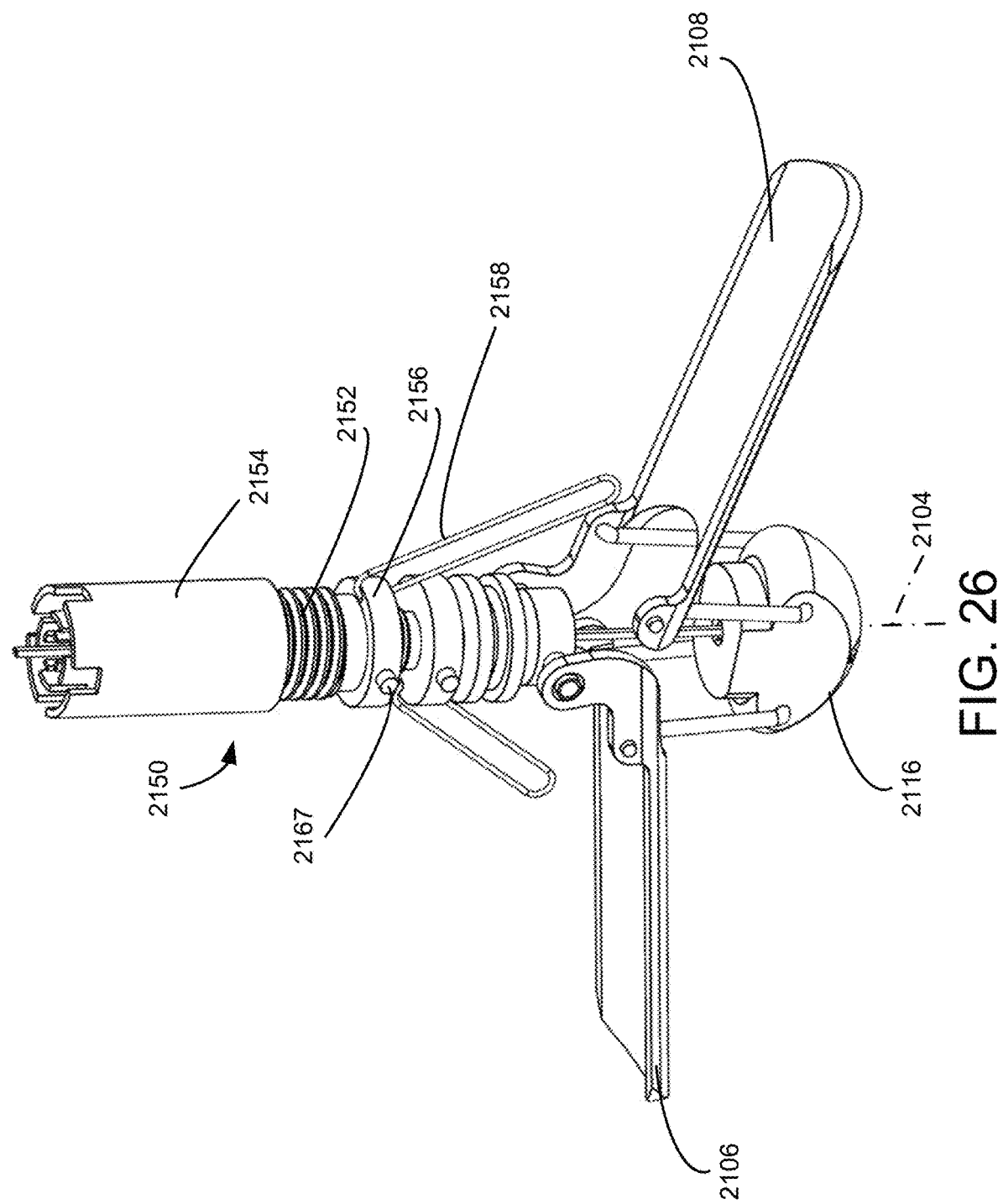
FIG. 26 illustrates the valve clip of FIG. 21 with various components removed to better illustrated a second retention member control mechanism.

FIG. 26 illustrates a retention member drive mechanism 2150 for retention member 2110 (omitted from FIG. 26 for clarity but shown in FIG. 21). Like retention member drive mechanism 2140, retention member drive mechanism 2150 includes a threaded shaft 2152 and a collar 2154. Threaded shaft 2152 is shown as externally threaded while collar 2154 is internally threaded such that rotation of collar 2154 translates threaded shaft 2152. Threaded shaft 2152 includes a distal hub 2156 through which a suture loop 2158 extends. Referring to FIG. 21, suture loop 2158 extends through holes defined through retention member 2112. For example, retention member 2112 includes a tab 2115 through which suture loop 2158 extends. In certain implementations, tab 2115 may be bent to extend perpendicular (e.g., proximally perpendicular in the arrangement shown in FIG. 21) to retention member 2112. Rotation of collar 2154 therefore can modify tension on suture loop 2158 to control abduction and adduction of retention member 2110 relative to longitudinal axis 2104.

Like distal hub 2146, distal hub 2156 may be configured or otherwise include features to facilitate alignment and prevent rotation of threaded shaft 2152 during operation. For example, distal hub 2156 generally has an outer diameter that corresponds to the inner diameter of tubular body 2102, facilitating alignment of retention member drive mechanism 2150 and threaded shaft 2152 within tubular body 2102. Distal hub 2156 further includes one or more protrusions shaped to be received within corresponding the longitudinal slots defined by tubular body 2102. For example, distal hub 2156 includes a first protrusion 2167 and a second protrusion 2169 (shown in FIG. 29) that are received within first slot 2149 and second slot 2151 of tubular body 2102, respectively. Accordingly, during rotation of collar 2154, the slots of tubular body 2102 prevent rotation of threaded shaft 2152 due to interference with the protrusions of distal hub 2156 while still permitting longitudinal travel of threaded shaft 2152.

Figure 27:
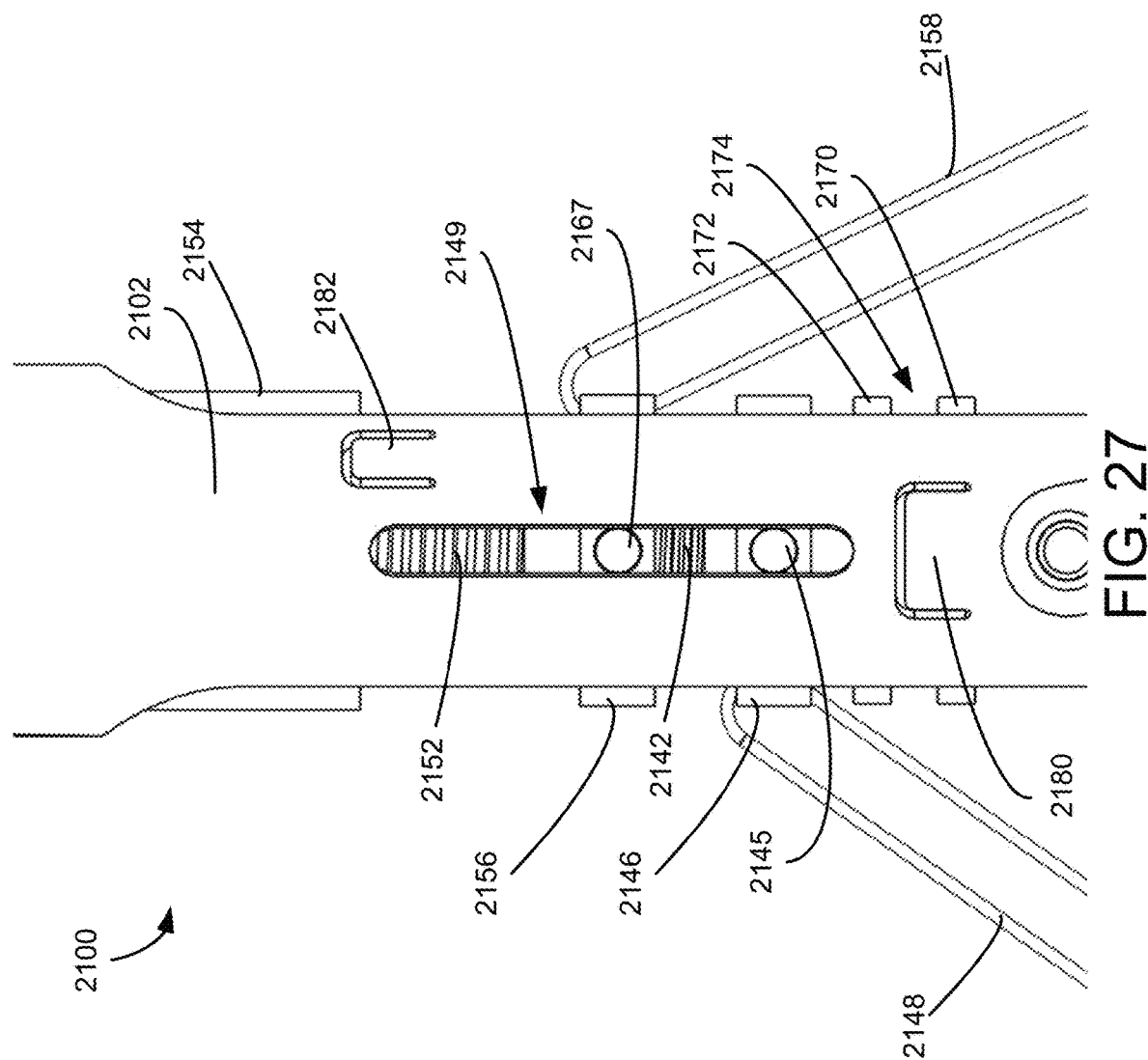
FIG. 27 is a detailed view of the valve clip of FIG. 21.

FIG. 27 is a detailed view of valve clip 2100 fully assembled. As illustrated, tubular body 2102 may include multiple integral tabs, such as a first distal tab 2180 and a first proximal tab 2182. Valve clip 2100 further includes a second distal tab 2181 (shown in FIG. 29) disposed opposite first distal tab 2180 and a second proximal tab (not shown in the figures) disposed opposite first proximal tab 2182. As illustrated, the tabs of tubular body 2102 may be formed by making U-shaped or similarly shaped cuts through tubular body 2102 (e.g., by laser cutting).

Prior to assembly of valve clip 2100, and as shown in FIG. 27, the tabs of tubular body 2102 are maintained in a first, unbent state. As the various internal components of valve clip 2100 are inserted into tubular body 2102, the tabs can be bent inwardly to retain the components, e.g., by preventing longitudinal translation. In certain implementations, the tabs of tubular body 2102 may be replaced by or supplemented with other retention mechanisms, such as, but not limited to set screws, clips, and clamps. In valve clip 2100, specifically, first distal tab 2180 and second distal tab 2181 are configured to retain collar 2134 of paddle control mechanism 2120 while first proximal tab 2182 and second proximal tab (not shown) are configured to retain collar 2154 of retention member drive mechanism 2150.

Figure 28:
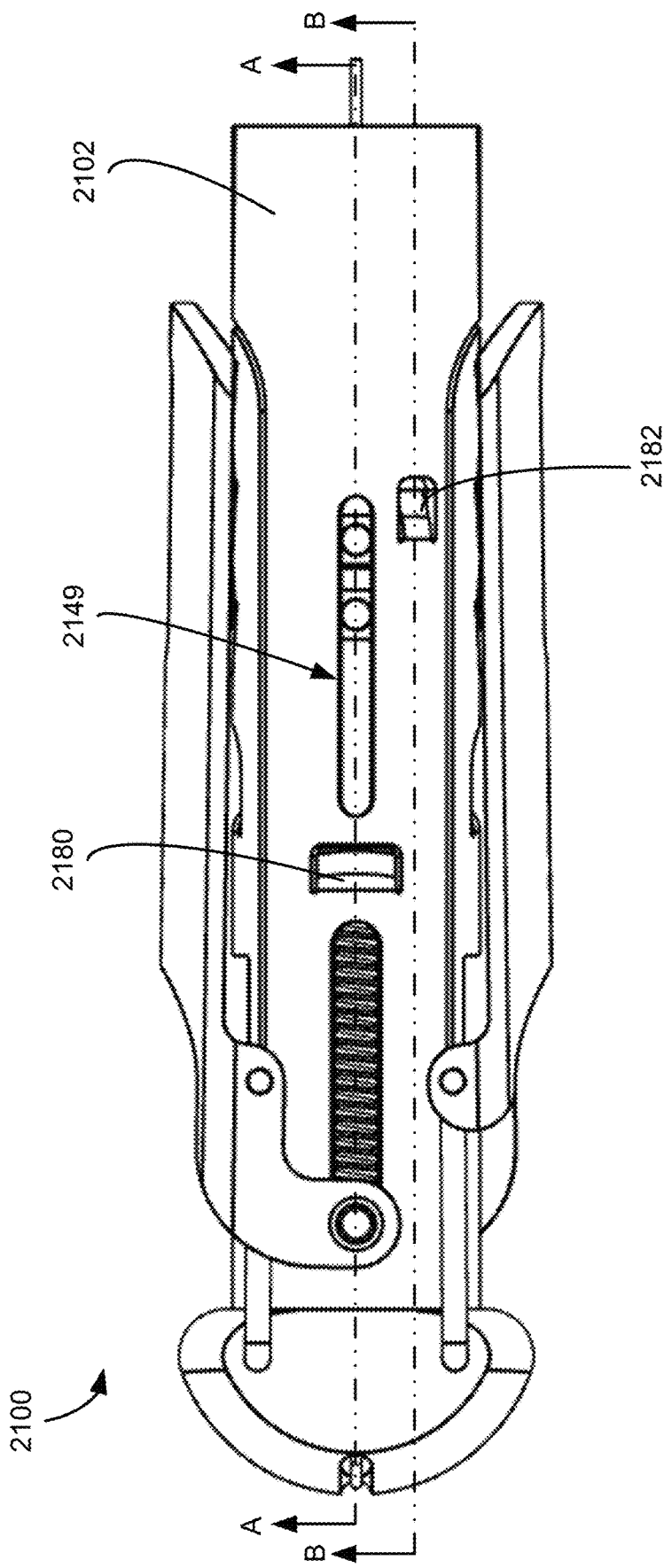
FIG. 28 is a side elevation view of the valve clip of FIG. 21.
Figure 29:
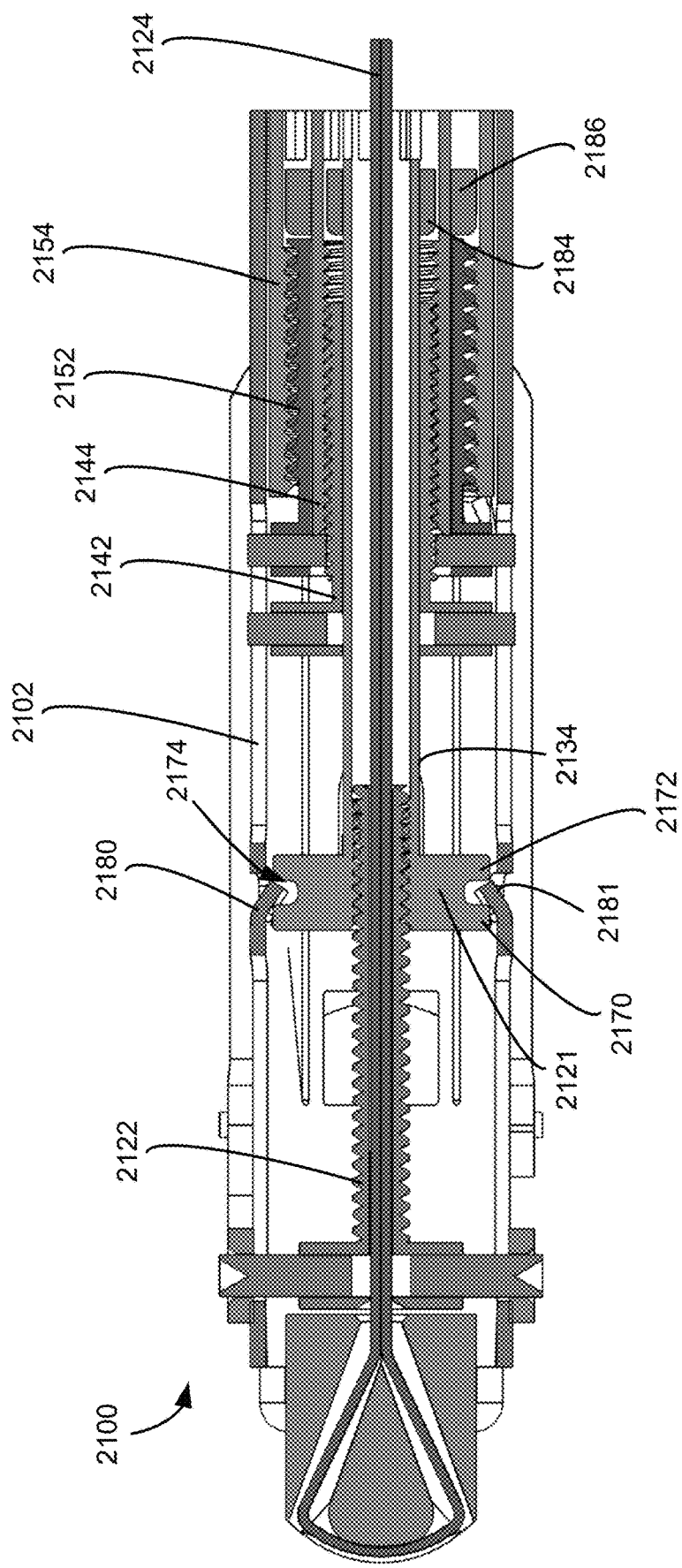
FIG. 29 is a first cross-sectional view of the valve clip of FIG. 21.
Figure 30:
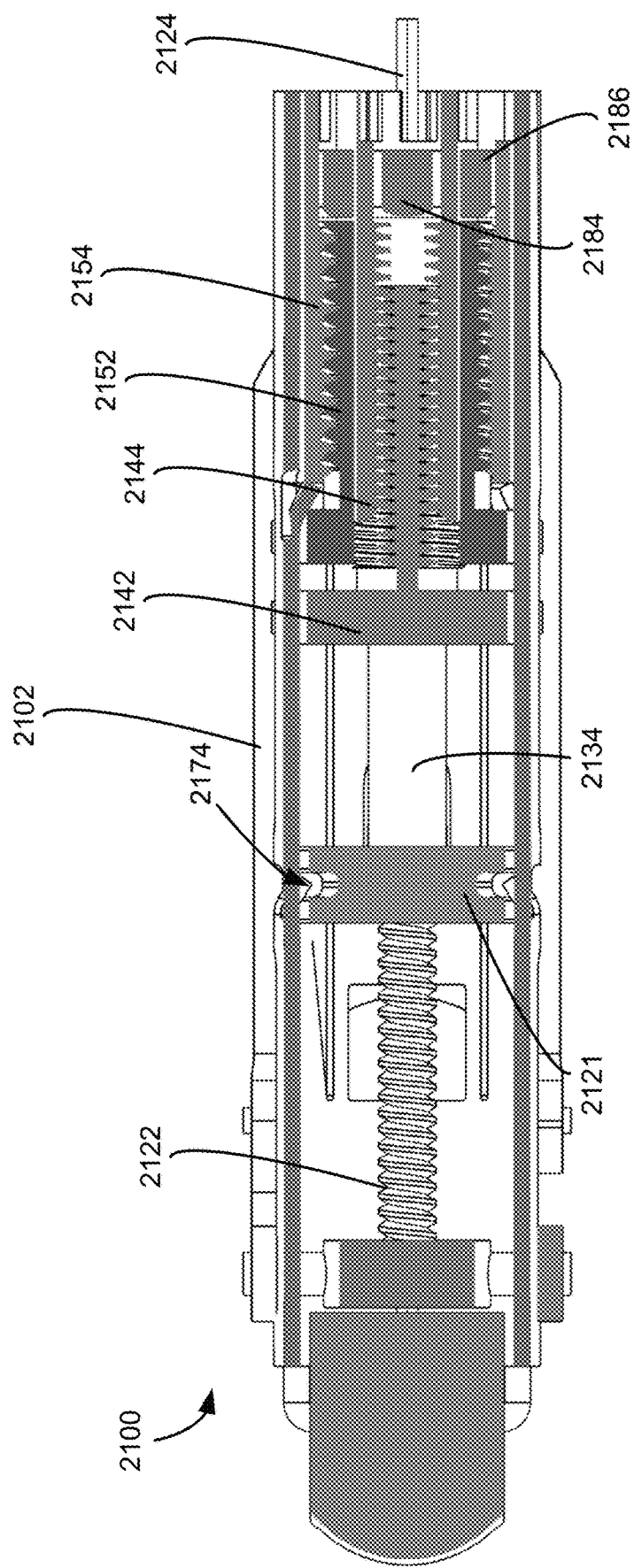
FIG. 30 is a second cross-sectional view of the valve clip of FIG. 21.

Use of the tabs of tubular body 2102 is further illustrated in FIGS. 28-30. FIG. 28 is a side elevation view of valve clip 2100 showing each of first distal tab 2180, second distal tab 2181, and first proximal tab 2182 bent inwardly to retain internal components of valve clip 2100.

FIG. 29 is a first cross-sectional view of valve clip 2100 along line A-A (shown in FIG. 27). As shown in FIG. 29, when valve clip 2100 is fully assembled and each of first distal tab 2180 and second distal tab 2181 are bent inwardly, first distal tab 2180 and second distal tab 2181 extend inwardly to retain collar 2134. More specifically, first distal tab 2180 and second distal tab 2181 extend inwardly between distal flange 2170 and proximal flange 2172 of distal hub 2146, which is disposed on a distal end of collar 2134. First distal tab 2180 and second distal tab 2181 therefore resist longitudinal translation of collar 2134 in either of the proximal or distal direction.

FIG. 30 is a second cross-section view of valve clip 2100 along line B-B (shown in FIG. 27). As shown in FIG. 30, when valve clip 2100 is fully assembled and first proximal tab 2182 is bent inwardly, first proximal tab 2182 extends inwardly at a location distal collar 2154. As previously noted, valve clip 2100 may also include one or more additional proximal tabs that may be similarly bent inwardly at locations distal collar 2154. By doing so, the proximal tabs resist longitudinal translation of collar 2154 in the distal direction.

Figure 31:
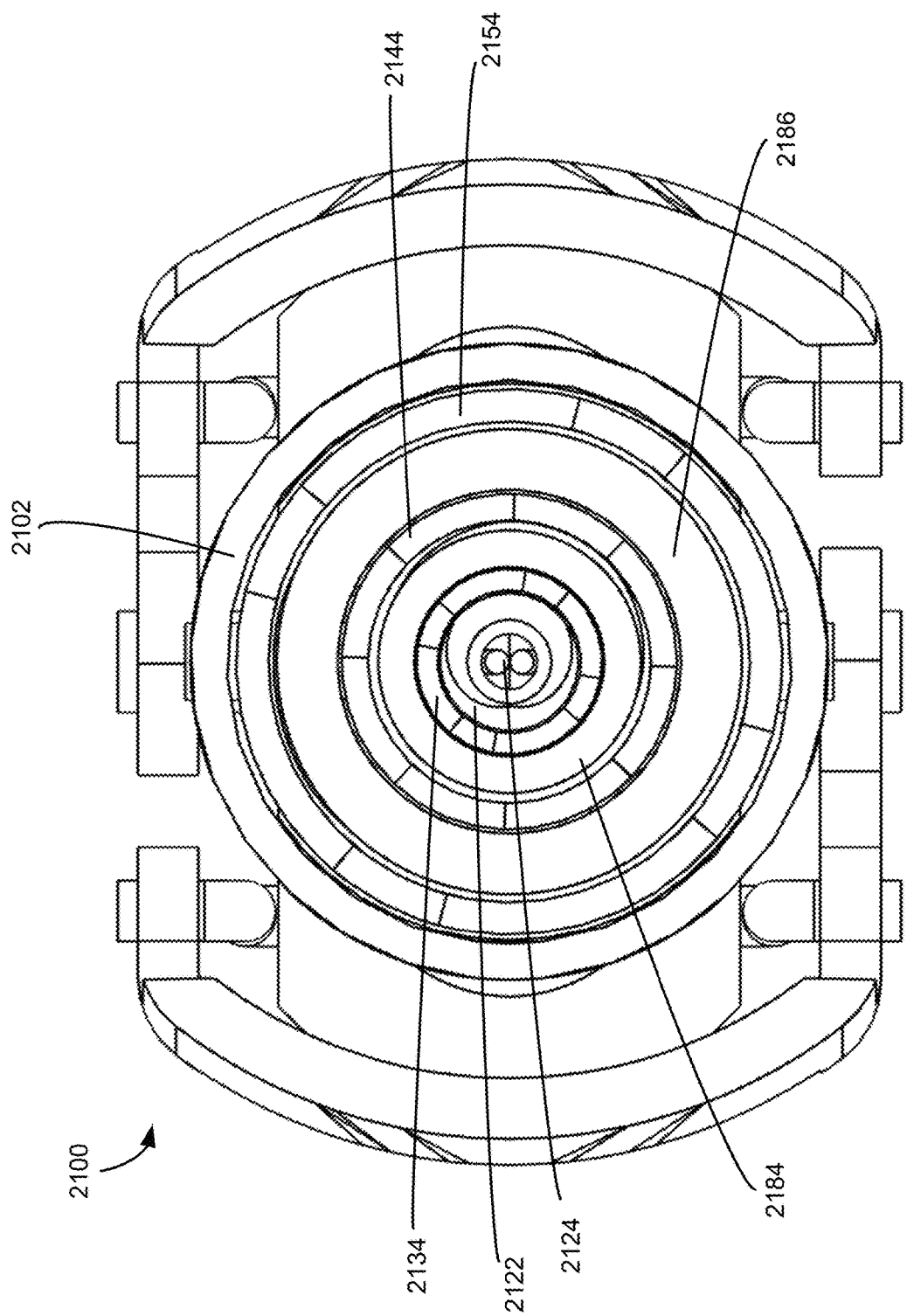
FIG. 31 is a proximal view of the valve clip of FIG. 21 in the closed configuration and illustrating arrangement of drive components of the valve clip.

In at least certain implementations, a series of rings located on a proximal portion of valve clip 2100 provide further retention of the internal components of valve clip 2100. In addition to being shown in FIGS. 29 and 30, FIG. 31 provides a proximal view of valve clip 2100 in the closed configuration and illustrating the arrangement of rings and internal drive components of valve clip 2100. In the view of FIG. 31, view of threaded shaft 2142 and threaded shaft 2152 are obstructed by distal hub 2146 and suture loop 2148, respectively.

Assembly of valve clip 2100 is described below in further detail; however, by way of introduction, valve clip 2100 includes an inner ring 2184 coupled to an external surface of collar 2134, e.g., by welding. Inner ring 2184 has an outer diameter that is generally larger than the inner diameter of the internal threads of collar 2144. Similarly, valve clip 2100 includes an outer ring 2186 coupled to an external surface of collar 2144, with outer ring 2186 having an outer diameter greater than the inner diameter of the internal threads of collar 2154. Accordingly, when valve clip 2100 is in a fully assembled state, first distal tab 2180 and second distal tab 2181 prevent longitudinal travel of collar 2134 in each of the distal and proximal directions. Longitudinal travel of collar 2144 is restricted in the proximal direction by inner ring 2184 and in the distal direction due to interference between outer ring 2186 (which is coupled to the outer surface of collar 2144) and collar 2154. Finally, longitudinal travel of collar 2154 in the distal direction is restricted by first proximal tab 2182 and the second proximal tab and in the proximal direction by outer ring 2186.

An example assembly process is now provided to further clarify the arrangement and coupling of the internal elements of valve clip 2100. To begin, an assembler obtains tubular body 2102. The assembler then inserts threaded shaft 2122 into tubular body 2102. The assembler inserts collar 2134 into tubular body 2102 and engages the internal threads of collar 2134 with the external threads of threaded shaft 2122 to couple collar 2134 to threaded shaft 2122. Following coupling of threaded shaft 2122 and collar 2134, the assembler longitudinally locates collar 2134 within tubular body 2102 to align gap 2174 with first distal tab 2180 and second distal tab 2181. The assembler then bends first distal tab 2180 and second distal tab 2181 inwardly into gap 2174 of collar 2134 to longitudinally retain collar 2134 within tubular body 2102.

With threaded shaft 2122 and collar 2134 secured within tubular body 2102, the assembler inserts threaded shaft 2142 into tubular body 2102 and over collar 2134. The assembler then inserts collar 2144 and engages the internal threads of collar 2144 with the external threads of threaded shaft 2142. With threaded shaft 2142 and collar 2144 now coupled, the assembler translates threaded shaft 2142 and collar 2144 distally to allow attachment of inner ring 2184 to the external surface of collar 2134, e.g., by welding. Following attachment of inner ring 2184 to collar 2134 threaded shaft 2142 and collar 2144 are generally able to longitudinally travel slide within tubular body 2102; however, inner ring 2184 prevents collar 2144 and threaded shaft 2142 from proximally exiting tubular body 2102.

Following insertion of threaded shaft 2142 and collar 2144, the assembler inserts threaded shaft 2152 over collar 2144. The assembler then inserts collars 2154 into tubular body 2102 and engages the outer threads of threaded shaft 2152 with the internal threads of collar 2154. The assembler longitudinally positions threaded shaft 2152 and collar 2154 such that first proximal tab 2182 and the second proximal tab (not shown) are longitudinally located between threaded shaft 2152 and collar 2154. The assembler bends the proximal tabs inwardly to prevent distal translation of collar 2154 and attaches outer ring 2186 to the external surface of collar 2144, e.g., by welding. As noted above, outer ring 2186 generally prevents both proximal translation of collar 2154 and distal translation of collar 2144.

With assembly of the internal components substantially complete, the assembler may then couple the internal components to their corresponding driven elements. For example, the assembler may couple threaded shaft 2122 to each of paddle 2106 and paddle 2108, distal hub 2146 to retention member 2110, and distal hub 2156 to retention member 2112. Alternatively, the assembler may couple the internal components to their corresponding driven elements during the internal assembly process as the assembler inserts each internal component into tubular body 2102.

Illustrative examples of the disclosure include:

Aspect 1: A valve repair device configured to attach to a native valve of a patient, the valve repair device including: a tubular body defining a longitudinal axis; a paddle supported by the tubular body; and a paddle control mechanism for moving the paddle, the paddle control mechanism including: a rotatable collar extending within the tubular body; and a shaft extending within the tubular body, threadedly engaged to the rotatable collar, and coupled to the paddle, wherein rotation of the rotatable collar in a first direction translates the shaft to abduct the paddle relative to the longitudinal axis and rotation of the rotatable collar in a second direction opposite the first direction translates the shaft to adduct the paddle relative to the longitudinal axis.

Aspect 2: The valve repair device of Aspect 1, wherein rotation of the rotatable collar in the first direction proximally translates the shaft and rotation of the rotatable collar in the second direction distally translates the shaft.

Aspect 3: The valve repair device of Aspect 1, wherein the paddle is a first paddle, the valve repair device further including a second paddle supported by the tubular body opposite the first paddle.

Aspect 4: The valve repair device of Aspect 3, wherein the shaft is further coupled to the second paddle, and wherein rotation of the rotatable collar in the first direction translates the shaft to abduct the second paddle relative to the longitudinal axis and rotation of the rotatable collar in the second direction translates the shaft to adduct the second paddle relative to the longitudinal axis.

Aspect 5: The valve repair device of Aspect 3, wherein the paddle control mechanism is a first paddle control mechanism, the valve repair device further including a second paddle control mechanism for moving the second paddle independently from the first paddle.

Aspect 6: The valve repair device of Aspect 5, wherein the second paddle control mechanism includes: a second rotatable collar extending within the tubular body; and a second shaft extending within the tubular body, wherein: the second shaft is threadedly engaged to the second rotatable collar and coupled to the second paddle, and rotation of the second rotatable collar in a first direction translates the second shaft to abduct the second paddle relative to the longitudinal axis and rotation of the second rotatable collar in a second direction opposite the first direction translates the second shaft to adduct the second paddle relative to the longitudinal axis.

Aspect 7: The valve repair device of Aspect 6, wherein each of the second rotatable collar and the second shaft are concentric with each of the shaft and the rotatable collar of the first paddle control mechanism.

Aspect 8: The valve repair device of Aspect 1 further including a retention member supported by the tubular body proximal the paddle and movable to grasp tissue between the retention member and the paddle.

Aspect 9: The valve repair device of Aspect 8, wherein the retention member includes a surface protrusion extending toward the paddle to positively engage tissue when tissue is grasped between the retention member and the paddle.

Aspect 10: The valve repair device of Aspect 8 further including a retention member control mechanism for moving the retention member independently of the paddle.

Aspect 11: The valve repair device of Aspect 10, wherein the retention member control mechanism includes: a second rotatable collar extending within the tubular body; and a second shaft extending within the tubular body, wherein: the second shaft is threadedly engaged to the second rotatable collar and coupled to the retention member, and rotation of the second rotatable collar in a first direction translates the second shaft to abduct the retention member relative to the longitudinal axis and rotation of the second rotatable collar in a second direction opposite the first direction translates the second shaft to adduct the retention member relative to the longitudinal axis.

Aspect 12: The valve repair device of Aspect 11, wherein the retention member is coupled to the second shaft by a suture loop.

Aspect 13: The valve repair device of Aspect 8, wherein the retention member is a first retention member, the paddle is a first paddle, and the valve repair device further includes: a second paddle; and a second retention member supported by the tubular body proximal the second paddle and movable to grasp tissue between the second retention member and the second paddle.

Aspect 14: The valve repair device of Aspect 13, further including: a first retention member control mechanism for moving the first retention member independently of the first paddle; and a second retention member control mechanism for moving the second retention member independently of the second paddle.

Aspect 15: The valve repair device of Aspect 14, wherein the second retention member control mechanism is operably independently of the first retention member control mechanism such that the first retention member is independently movable of the second retention member.

Aspect 16: The valve repair device of Aspect 14, wherein the first retention member control mechanism includes: a second rotatable collar extending within the tubular body; and a second shaft extending within the tubular body, wherein: the second shaft is threadedly engaged to the second rotatable collar and coupled to the retention member, and rotation of the second rotatable collar in a first direction translates the second shaft to abduct the second retention member relative to the longitudinal axis and rotation of the second rotatable collar in a second direction opposite the first direction translates the second shaft to adduct the second retention member relative to the longitudinal axis.

Aspect 17: The valve repair device of Aspect 16, wherein the first retention member control mechanism includes: a third rotatable collar extending within the tubular body; and a third shaft extending within the tubular body, wherein: the third shaft is threadedly engaged to the third rotatable collar and coupled to the second retention member, and rotation of the third rotatable collar in a first direction translates the third shaft to abduct the second retention member relative to the longitudinal axis and rotation of the third rotatable collar in a second direction opposite the first direction translates the third shaft to adduct the second retention member relative to the longitudinal axis.

Aspect 18: The valve repair device of Aspect 8, wherein the retention member is biased to abduct relative to the longitudinal axis.

Aspect 19: The valve repair device of Aspect 1 further including a nose coupled to a distal end of the tubular body, wherein the nose defines distal openings in communication with an internal volume of the tubular body to facilitate retention of the valve repair device on a tether passed through the distal openings.

Aspect 20: The valve repair device of Aspect 1 further including: a nose coupled to a distal end of the tubular body; and a link rotatably coupled to each of the nose and the paddle.

Aspect 21: The valve repair device of Aspect 1 further including a nose coupled to a distal end of the tubular body, wherein the nose includes a pair of distally opening holes configured to permit looping of a tether through the pair of holes to retain the valve repair device on a delivery tool.

Aspect 22: A valve repair device configured to attach to a native valve of a patient, the valve repair device including: a first paddle and a second paddle, wherein the first paddle and the second paddle are movable between an open position and a closed position; a first paddle control mechanism for moving the first paddle, the first paddle control mechanism including: a first rotatable collar; and a first threaded shaft engaged with the first rotatable collar and coupled to the first paddle such that rotation of the first rotatable collar translates the first threaded shaft and moves the first paddle between the open position and the closed position; and a second paddle control mechanism for moving the second paddle independently of the first paddle, wherein the second paddle control mechanism includes: a second rotatable collar; and a second threaded shaft engaged with the second rotatable collar and coupled to the second paddle such that rotation of the second rotatable collar translates the second threaded shaft and moves the second paddle between the open position and the closed position.

Aspect 23: The valve repair device of Aspect 22, wherein the first rotatable collar and the second rotatable collar are concentric.

Aspect 24: The valve repair device of Aspect 22, wherein the first threaded shaft and the second threaded shaft are concentric.

Aspect 25: The valve repair device of Aspect 22, wherein the first rotatable collar, the first threaded shaft, the second rotatable collar, and the second threaded shaft are concentric.

Aspect 26: The valve repair device of Aspect 22, further including: a tubular body within which the first threaded shaft extends, the tubular body defining a longitudinal slot; and a pin coupling the first threaded shaft to the first paddle, wherein the pin extends laterally from the first threaded shaft through the longitudinal slot defined by the tubular body.

Aspect 27: The valve repair device of Aspect 22, further including: a pin coupling the second threaded shaft to the second paddle, wherein the first threaded shaft defines a longitudinal slot and the pin extends laterally from the second threaded shaft through the longitudinal slot defined by first threaded shaft.

Aspect 28: The valve repair device of Aspect 22, further including: a body within which each of the first threaded shaft and the second threaded shaft extends, the body defining a first longitudinal slot; a first pin coupling the first threaded shaft to the first paddle; and a second pin coupling the second threaded shaft to the second paddle, wherein: the first pin extends laterally from the first threaded shaft through the first longitudinal slot, the first threaded shaft defines a second longitudinal slot, and the second pin extends laterally from the second threaded shaft through the second longitudinal slot.

Aspect 29: The valve repair device of Aspect 22, further including: a first retention member movable between an open position and a closed position to secure a first valve leaflet between the first retention member and the first paddle; and a second retention member movable between an open position and a closed position to secure a second valve leaflet between the second retention member and the second paddle, wherein each of the first retention member and the second retention member is biased toward the open position.

Aspect 30: The valve repair device of Aspect 22, further including: a first retention member movable between an open position and a closed position to secure a first valve leaflet between the first retention member and the first paddle; and a second retention member movable between an open position and a closed position to secure a second valve leaflet between the second retention member and the second paddle, wherein each of the first retention member and the second retention member are independently movable by a respective control mechanism.

Aspect 31: The valve repair device of Aspect 22, further including a body within which the first rotatable collar, the first threaded shaft, the second rotatable collar, and the second threaded shaft are disposed and concentrically mounted, the body including a nose disposed at a distal end of the body, wherein: the first rotatable collar, the first threaded shaft, the second rotatable collar, and the second threaded shaft collectively define a tether lumen, and the nose defines tether through holes, such that a tether of a delivery tool is extendable through the tether lumen and the tether through holes to couple the valve repair device to the delivery tool.

Aspect 32: The valve repair device of Aspect 22, further including a body within which the first rotatable collar, the first threaded shaft, the second rotatable collar, and the second threaded shaft are disposed, the body including a nose disposed at a distal end of the body, wherein: the first paddle control mechanism further includes a first link extending between the first paddle and the nose such that proximal translation of the first threaded shaft transitions the first paddle toward the closed position and distal translation of the first threaded shaft transitions the first paddle toward the open position, and the second paddle control mechanism further includes a second link extending between the second paddle and the nose such that proximal translation of the second threaded shaft transitions the second paddle toward the closed position and distal translation of the second threaded shaft transitions the second paddle toward the open position.

Aspect 33: The valve repair device of Aspect 22, wherein: the first rotatable collar is disposed radially outward of the first threaded shaft, the first threaded shaft is disposed radially outward of the second rotatable collar, and the second rotatable collar is disposed radially outward of the second threaded shaft.

Aspect 34: The valve repair device of Aspect 22, wherein: each of the first rotatable collar and the second rotatable collar is internally threaded, and each of the first threaded shaft and the second threaded shaft is externally threaded.

Aspect 35: A valve repair device configured to attach to a native valve of a patient, the valve repair device including: a body; a first paddle and a second paddle, wherein the first and second paddles are movable between an open position and a closed position; a paddle control mechanism for simultaneously moving the first paddle and the second paddle, the paddle control mechanism including: a rotatable collar; and a threaded shaft disposed radially inward of and engaged with the rotatable collar and coupled to each of the first paddle and the second paddle such that rotation of the rotatable collar translates the threaded shaft and moves the first paddle and the second paddle between the open position and the closed position; a first retention member movable between an open position and a closed position to secure a first valve leaflet between the first retention member and the first paddle; and a second retention member movable between an open position and a closed position to secure a second valve leaflet between the second retention member and the second paddle.

Aspect 36: The valve repair device of Aspect 35 further including: a first pin coupling the threaded shaft to the first paddle, wherein: the body defines a first longitudinal slot, and the first pin extends laterally from the threaded shaft through the first longitudinal slot defined by the body; and a second pin coupling the threaded shaft to the second paddle, wherein: the body defines a second longitudinal slot, and the second pin extends laterally from the threaded shaft through the second longitudinal slot.

Aspect 37: The valve repair device of Aspect 35, further including a nose disposed at a distal end of the body, wherein the threaded shaft defines a tether lumen, and the nose defines tether through holes such that a tether of a delivery tool is extendable through the tether lumen and the tether through holes to couple the valve repair device to the delivery tool.

Aspect 38: The valve repair device of Aspect 35, further including: a nose disposed at a distal end of the body; a first link extending from the first paddle to the nose; and a second link extending from the second paddle to the nose.

Aspect 39: The valve repair device of Aspect 35, wherein each of the first retention member and the second retention member is biased into the open position.

Aspect 40: The valve repair device of Aspect 35, wherein each of the first retention member and the second retention member is independently movable between the open position and the closed position.

Aspect 41: The valve repair device of Aspect 35, wherein: the rotatable collar is internally threaded, and the threaded shaft is externally threaded.

Aspect 42: A method of valve repair including: delivering a valve repair implant to an atrium of a patient heart, the valve repair implant including: a tubular body defining a longitudinal axis; a paddle supported by the tubular body; a paddle control mechanism for moving the paddle, the paddle control mechanism including: a rotatable collar extending within the tubular body; a shaft extending within the tubular body, threadedly engaged to the rotatable collar, and coupled to the paddle, wherein rotation of the rotatable collar in a first direction translates the shaft to abduct the paddle relative to the longitudinal axis and rotation of the rotatable collar in a second direction opposite the first direction translates the shaft to adduct the paddle relative to the longitudinal axis; and a retention member supported by the tubular body proximal the paddle; disposing the paddle on a ventricular side of a valve of the patient heart; opening the valve repair implant by abducting each of the paddle and the retention member; and disposing a leaflet of the valve between the paddle and the retention member.

Aspect 43: The method of Aspect 42, wherein abducting the paddle includes rotating the rotatable collar.

Aspect 44: The method of Aspect 42, wherein the retention member is biased into abduction.

Aspect 45: The method of Aspect 42, wherein the valve repair implant further includes a retention member control mechanism configured to selectively abduct and adduct the retention member.

Aspect 46: The method of Aspect 42, wherein: the valve repair implant further includes a retention member control mechanism configured to selectively abduct and adduct the retention member, the retention member control mechanism including: a second rotatable collar extending within the tubular body, and a second shaft extending within the tubular body, wherein the second shaft is threadedly engaged to the second rotatable collar and coupled to the retention member, and rotation of the second rotatable collar in a first direction translates the second shaft to abduct the retention member relative to the longitudinal axis and rotation of the second rotatable collar in a second direction opposite the first direction translates the second shaft to adduct the retention member relative to the longitudinal axis, and opening the valve repair implant includes rotating the second rotatable collar to abduct the retention member.

Aspect 47: The method of Aspect 42, wherein the valve repair implant further includes a second paddle simultaneously operable with the first paddle using the paddle control mechanism, and wherein opening the vale repair implant further includes abducting the second paddle by rotating the rotatable collar.

Aspect 48: The method of Aspect 42, wherein the valve repair implant further includes a second paddle and a second paddle control mechanism for abducting and adducting the second paddle independent of the first paddle, and wherein opening the vale repair implant further includes abducting the second paddle using the second paddle control mechanism.

Aspect 49: The method of Aspect 42, wherein: the valve repair implant further includes: a second paddle, and a second retention member supported by the tubular body proximal the second paddle, opening the valve repair implant includes abducting each of the second paddle and the second retention member, and the method further includes disposing a second leaflet of the valve between the second paddle and the second retention member.

Aspect 50: A valve repair device configured to attach to a native valve of a patient, the valve repair device including: a tubular body; a first paddle and a second paddle, wherein the first and second paddles are movable between an open position and a closed position; a paddle control mechanism for simultaneously moving the first paddle and the second paddle, the paddle control mechanism including: a paddle collar; and a paddle threaded shaft disposed radially inward of and engaged with the paddle collar and coupled to each of the first paddle and the second paddle such that rotation of the paddle collar translates the paddle threaded shaft and moves the first paddle and the second paddle between the open position and the closed position; a first retention member movable between an open position and a closed position to secure a first valve leaflet between the first retention member and the first paddle; a first retention member control mechanism for moving the first retention member between the open position and the closed position; a second retention member movable between an open position and a closed position to secure a second valve leaflet between the second retention member and the second paddle; and a second retention member control mechanism for moving the second retention member between the open position and the closed position.

Aspect 51: The valve repair device of Aspect 50, wherein the tubular body includes inwardly extending tabs configured to longitudinally constrain the paddle collar.

Aspect 52: The valve repair device of Aspect 51, wherein the paddle collar includes a distal hub having a proximal flange, a distal flange, and a gap disposed between the proximal flange and the distal flange, and wherein the inwardly extending tabs extend into the gap.

Aspect 53: The valve repair device of Aspect 50, wherein the first retention member control mechanism includes: a first retention member collar; and a first retention member threaded shaft disposed radially inward of and engaged with the first retention member collar and coupled to the first retention member such that rotation of the first retention member collar translates the first retention member threaded shaft and moves the first retention member between the open position and the closed position, wherein each of the paddle collar and the paddle threaded shaft are disposed radially inward of the first retention member collar and the first retention member threaded shaft.

Aspect 54: The valve repair device of Aspect 53, wherein the second retention member control mechanism includes: a second retention member collar; and a second retention member threaded shaft disposed radially inward of and engaged with the second retention member collar and coupled to the second retention member such that rotation of the second retention member collar translates the second retention member threaded shaft and moves the second retention member between the open position and the closed position, wherein each of the first retention member collar and the first retention member threaded shaft are disposed radially inward of the first retention member collar and the first retention member threaded shaft.

Aspect 55: The valve repair device of Aspect 54, wherein each of the paddle collar, the first retention member collar, and the second retention member collar are longitudinally constrained relative to the tubular body.

Aspect 56: The valve repair device of Aspect 55, wherein the tubular body includes an inwardly extending tab that longitudinally constrains the paddle collar in each of a proximal and a distal direction.

Aspect 57: The valve repair device of Aspect 55, wherein the tubular body includes an inwardly extending tab that longitudinally constrains the second retention member collar in at least a distal direction.

Aspect 58: The valve repair device of Aspect 55 further including a ring coupled to an exterior surface of the paddle collar, the ring extending between the paddle collar and the first retention member collar proximal the first retention member threaded shaft.

Aspect 59: The valve repair device of Aspect 55 further including a ring coupled to an exterior surface of the first retention member collar, the ring extending between the first retention member collar and the second retention member collar proximal the second retention member threaded shaft.

Aspect 60: The valve repair device of Aspect 55, further including: a first ring coupled to an exterior surface of the paddle collar, the first ring extending between the paddle collar and the first retention member collar proximal the first retention member threaded shaft; and a second ring coupled to an exterior surface of the first retention member collar, the second ring extending between the first retention member collar and the second retention member collar proximal the second retention member threaded shaft.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e., "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A valve repair device configured to attach to a native valve of a patient, the valve repair device comprising:
   a tubular body defining a longitudinal axis;
   a paddle supported by the tubular body;
   a paddle control mechanism for moving the paddle, the paddle control mechanism including:
      a rotatable paddle collar extending within the tubular body; and
      a paddle shaft extending within the tubular body, wherein:
         the paddle shaft is threadedly engaged to the rotatable paddle collar and coupled to the paddle,
         the rotatable paddle collar is configured to rotate to translate the paddle shaft, and
         the paddle shaft is configured to translate to change abduction of the paddle relative to the longitudinal axis;
   a retention member supported by the tubular body proximal the paddle; and
   a retention member control mechanism for moving the retention member to facilitate capture of a valve leaflet between the paddle and the retention member, the retention member control mechanism including:
      a rotatable retention member collar extending within the tubular body; and
      a retention member shaft extending within the tubular body, wherein:
         the retention member shaft is threadedly engaged to the rotatable retention member collar and coupled to the retention member,
         the rotatable retention member collar is configured to rotate to translate the retention member shaft, and the retention member shaft is configured to translate to change abduction of the retention member relative to the longitudinal axis.

2. The valve repair device of claim 1, wherein the rotatable paddle collar and the rotatable retention member collar are concentric within the tubular body.

3. The valve repair device of claim 1, wherein the rotatable paddle collar and the rotatable retention member collar are concentric within the tubular body and the rotatable paddle collar is radially inward of the rotatable retention member collar.

4. The valve repair device of claim 1, wherein the rotatable paddle collar is configured to rotate in a first direction to drive the paddle shaft distally and abduct the paddle relative to the longitudinal axis and is further configured to rotate in a second direction opposite the first direction to drive the paddle shaft proximally and adduct the paddle.

5. The valve repair device of claim 1, wherein the rotatable retention member collar is configured to rotate in a first direction to drive the retention member shaft distally and abduct the retention member and is further configured to rotate in a second direction opposite the first direction to drive the retention member shaft proximally and adduct the retention member.

6. The valve repair device of claim 1, wherein the paddle is a first paddle, the valve repair device further comprising a second paddle supported by the tubular body, wherein:
the paddle shaft is further coupled to the second paddle, and
the rotatable paddle collar is further configured to rotate to translate the paddle shaft to simultaneously change each of abduction of the second paddle and abduction of the first paddle relative to the longitudinal axis.

7. The valve repair device of claim 1, wherein the paddle is a first paddle, the paddle control mechanism is a first paddle control mechanism, the rotatable paddle collar is a first rotatable paddle collar, and the paddle shaft is a first paddle shaft, the valve repair device further comprising:
a second paddle supported by the tubular body; and
a second paddle control mechanism for moving the second paddle, the second paddle control mechanism including:
a second rotatable paddle collar extending within the tubular body; and
a second paddle shaft extending within the tubular body, wherein:
the second paddle shaft is threadedly engaged to the second rotatable paddle collar and coupled to the second paddle,
the second rotatable paddle collar is configured to translate the second paddle shaft, and
the second paddle shaft is configured to translate to change abduction of the second paddle relative to the longitudinal axis independent of changing abduction of the first paddle relative to the longitudinal axis.

8. The valve repair device of claim 1, wherein the retention member is a first retention member, the valve repair device further comprising a second retention member supported by the tubular body, wherein:
the retention member shaft is further coupled to the second retention member, and
the rotatable retention member collar is further configured to rotate to translate the retention member shaft to simultaneously change each of abduction of the second retention member and abduction of the first retention member relative to the longitudinal axis.

9. The valve repair device of claim 1, wherein the retention member is a first retention member, the retention member control mechanism is a first retention member control mechanism, the rotatable retention member collar is a first rotatable retention member collar, and the retention member shaft is a first retention member shaft, the valve repair device further comprising:
a second retention member supported by the tubular body; and
a second retention member control mechanism for moving the second retention member, the second retention control mechanism including:
a second rotatable retention member collar extending within the tubular body; and
a second retention member shaft extending within the tubular body, wherein:
the second retention member shaft is threadedly engaged to the second rotatable retention member collar and coupled to the second retention member,
the second rotatable retention member collar is configured to translate the second retention member shaft, and
the second retention member shaft is configured to translate to change abduction of the second retention member relative to the longitudinal axis independent of changing abduction of the first retention member relative to the longitudinal axis.

10. The valve repair device of claim 1, wherein the retention member includes a distal face including a surface feature extending from the distal face and configured to engage the valve leaflet.

11. The valve repair device of claim 1, wherein the retention member is coupled to the retention member shaft by a suture loop.

12. A valve repair device configured to attach to a native valve of a patient, the valve repair device comprising:
a tubular body defining a longitudinal axis;
a first paddle supported by the tubular body;
a second paddle supported by the tubular body;
a paddle control mechanism for simultaneously changing abduction of the first paddle and the second paddle relative to the longitudinal axis;
a first retention member supported by the tubular body proximal the first paddle;
a retention member control mechanism for moving the first retention member to facilitate capture of a valve leaflet between the first paddle and the first retention member, the retention member control mechanism including:
a retention member collar extending within the tubular body; and
a retention member shaft extending within the tubular body, wherein the retention member shaft is threadedly engaged to the retention member collar and coupled to the first retention member, the retention member collar rotatable to selectively translate the retention member shaft to change abduction of the first retention member relative to the longitudinal axis; and
a second retention member supported by the tubular body proximal the second paddle, wherein the second retention member is movable to change abduction of the second retention member relative to the longitudinal axis.

13. The valve repair device of claim 12, wherein the second retention member is independently movable from the first retention member.

14. The valve repair device of claim 12, wherein the retention member control mechanism is a first retention member control mechanism, the retention member collar is a first retention member collar, and the retention member shaft is a first retention member shaft, the valve repair device further comprising:
- a second retention member control mechanism for moving the second retention member independently from the first retention member, the second retention control mechanism including:
  - a second retention member collar extending within the tubular body; and
  - a second retention member shaft extending within the tubular body, wherein the second retention member shaft is threadedly engaged to the second retention member collar and coupled to the second retention member, the second retention member collar rotatable to selectively translate the second retention member shaft to change abduction of the second retention member relative to the longitudinal axis.

15. The valve repair device of claim 14, wherein the first retention member is concentric with the second retention member collar.

16. The valve repair device of claim 12, wherein the second retention member is movable simultaneously with the first retention member.

17. The valve repair device of claim 12, wherein:
- the retention member shaft is further coupled to the second retention member, and
- the retention member collar is rotatable to translate the retention member shaft to simultaneously change abduction of each of the first retention member and the second retention member relative to the longitudinal axis.

18. A valve repair device configured to attach to a native valve of a patient, the valve repair device comprising:
- a tubular body defining a longitudinal axis;
- a paddle supported by the tubular body, the paddle movable to change abduction of the paddle relative to the longitudinal axis;
- a retention member supported by the tubular body proximal the paddle, the retention member movable to change abduction of the retention member relative to the longitudinal axis; and
- a control mechanism for moving one of the paddle and the retention member, the control mechanism including:
  - a rotatable collar extending within the tubular body; and
  - a shaft extending within the tubular body, threadedly engaged to the rotatable collar, and coupled to one of the paddle and the retention member, wherein:
    - the rotatable collar is configured to rotate to translate the shaft, and
    - the shaft is configured to translate to change abduction of the one of the paddle and the retention member relative to the longitudinal axis to facilitate capture of a valve leaflet between the paddle and the retention member.

19. The valve repair device of claim 18, wherein the paddle is a first paddle and the retention member is a first retention member, the valve repair device further comprising:
- a second paddle supported by the tubular body, the second paddle movable to change abduction of the second paddle relative to the longitudinal axis; and
- a second retention member supported by the tubular body proximal the second paddle, the second retention member movable to change abduction of the second retention member relative to the longitudinal axis.

20. The valve repair device of claim 18, wherein the retention member is biased into abduction.

* * * * *